(12) United States Patent
Shimasaki et al.

(10) Patent No.: US 10,253,291 B2
(45) Date of Patent: Apr. 9, 2019

(54) CULTURE VESSEL

(71) Applicants: KANAZAWA MEDICAL UNIVERSITY, Ishikawa (JP); SHINKO CHEMICAL CO., LTD., Ishikawa (JP)

(72) Inventors: Takeo Shimasaki, Ishikawa (JP); Yumiko Kitano, Ishikawa (JP); Hideki Yamada, Ishikawa (JP)

(73) Assignees: KANAZAWA MEDICAL UNIVERSITY, Ishikawa (JP); SHINKO CHEMICAL CO., LTD., Ishikawa (JP)

( * ) Notice: Subject to any disclaimer, the term of this patent is extended or adjusted under 35 U.S.C. 154(b) by 457 days.

(21) Appl. No.: 14/901,775

(22) PCT Filed: Jul. 31, 2014

(86) PCT No.: PCT/JP2014/070209
§ 371 (c)(1),
(2) Date: Dec. 29, 2015

(87) PCT Pub. No.: WO2015/019938
PCT Pub. Date: Feb. 12, 2015

(65) Prior Publication Data
US 2016/0369224 A1 Dec. 22, 2016

(30) Foreign Application Priority Data

Aug. 8, 2013 (JP) .................................. 2013-164907
Jul. 1, 2014 (JP) .................................. 2014-135535

(51) Int. Cl.
*C12M 1/00* (2006.01)
*C12M 1/12* (2006.01)
(Continued)

(52) U.S. Cl.
CPC ............ *C12M 41/46* (2013.01); *C12M 23/04* (2013.01); *C12M 23/22* (2013.01); *C12M 23/34* (2013.01);
(Continued)

(58) Field of Classification Search
CPC ...... C12M 23/22; C12M 23/58; C12M 25/02; C12M 41/46; C12M 23/04; C12M 23/34; C12M 23/44
See application file for complete search history.

(56) References Cited

U.S. PATENT DOCUMENTS 3,221,878 A    12/1965   Brett
4,717,661 A *   1/1988   McCormick et al. ... C12Q 1/22
                                                                                          435/287.4
(Continued)

FOREIGN PATENT DOCUMENTS

CN       202849409      4/2013
CN       203112849      8/2013
(Continued)

OTHER PUBLICATIONS

Office Action dated Sep. 12, 2017 in corresponding Chinese Application No. 201480035657.X, with English translation.
(Continued)

*Primary Examiner* — Gautam Prakash
(74) *Attorney, Agent, or Firm* — Wenderoth, Lind & Ponack, L.L.P.

(57) ABSTRACT

The present invention relates to a culture vessel which can be broadly applied to culture, regeneration, manufacture, observation and the like of targets such as cells, organs, and microorganisms. In the culture vessel of the present invention, a first vessel 10 and a second vessel 20 each being a close-bottom, open-top vessel are provided. In the first vessel 10 and the second vessel 20, a sideways-facing
(Continued)

opening 12 and a sideways-facing opening 22 are formed. The opening 12 and the opening 22 communicate in a watertight manner when the openings 12, 22 are connected face to face.

9 Claims, 22 Drawing Sheets

(51) Int. Cl.
 *C12M 1/34* (2006.01)
 *C12M 3/00* (2006.01)
(52) U.S. Cl.
 CPC ............ *C12M 23/44* (2013.01); *C12M 23/58* (2013.01); *C12M 25/02* (2013.01)

(56) References Cited

U.S. PATENT DOCUMENTS

| | | | |
|---|---|---|---|
| 4,927,764 A * | 5/1990 | Lyman et al. | ............ B01L 3/08 215/10 |
| 5,583,037 A * | 12/1996 | Mussi et al. | ........... C12M 25/04 422/501 |
| 5,602,028 A | 2/1997 | Minchinton | |
| 2005/0101010 A1 | 5/2005 | Li | |
| 2006/0147903 A1 | 7/2006 | Li | |
| 2007/0172814 A1 | 7/2007 | Li | |
| 2007/0172944 A1 | 7/2007 | Li | |
| 2007/0178441 A1 | 8/2007 | Li | |
| 2010/0273258 A1 | 10/2010 | Lannutti et al. | |
| 2011/0117541 A1 | 5/2011 | Li | |

FOREIGN PATENT DOCUMENTS

| | | |
|---|---|---|
| JP | 5-219934 | 8/1993 |
| JP | 2006-101797 | 4/2006 |
| JP | 2007-215472 | 8/2007 |
| JP | 4609799 | 1/2011 |
| WO | 2010/124207 | 10/2010 |

OTHER PUBLICATIONS

International Search Report dated Nov. 4, 2014 in International Application No. PCT/JP2014/070209.
Office Action dated Dec. 28, 2016 in corresponding Chinese Application No. 201480035657.X, with English translation.
Extended European Search Report dated Nov. 14, 2016 in corresponding European Application No. 14834552.3.
Office Action dated May 31, 2018 in Australian Application No. 2014303580.

\* cited by examiner

[Fig.1]
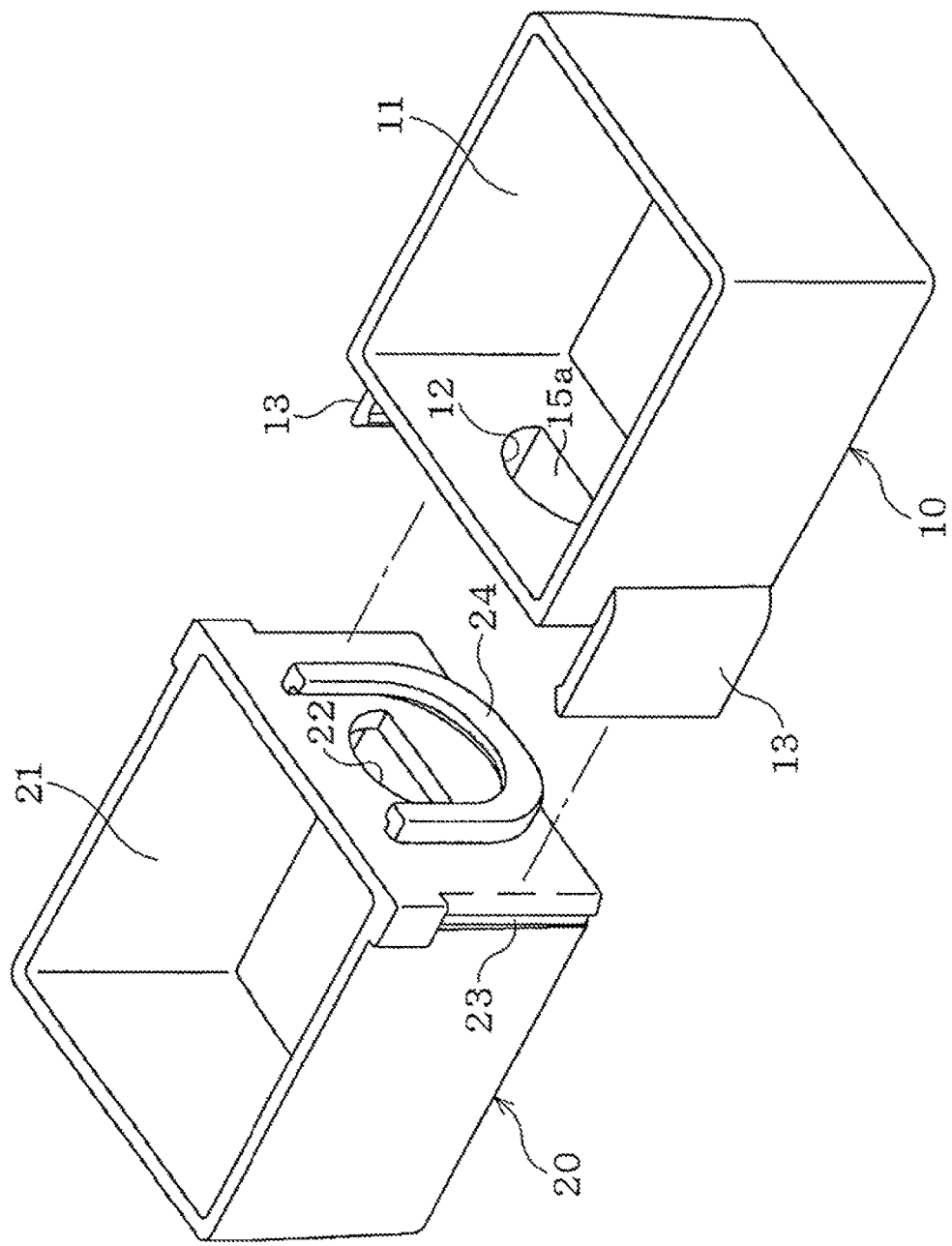

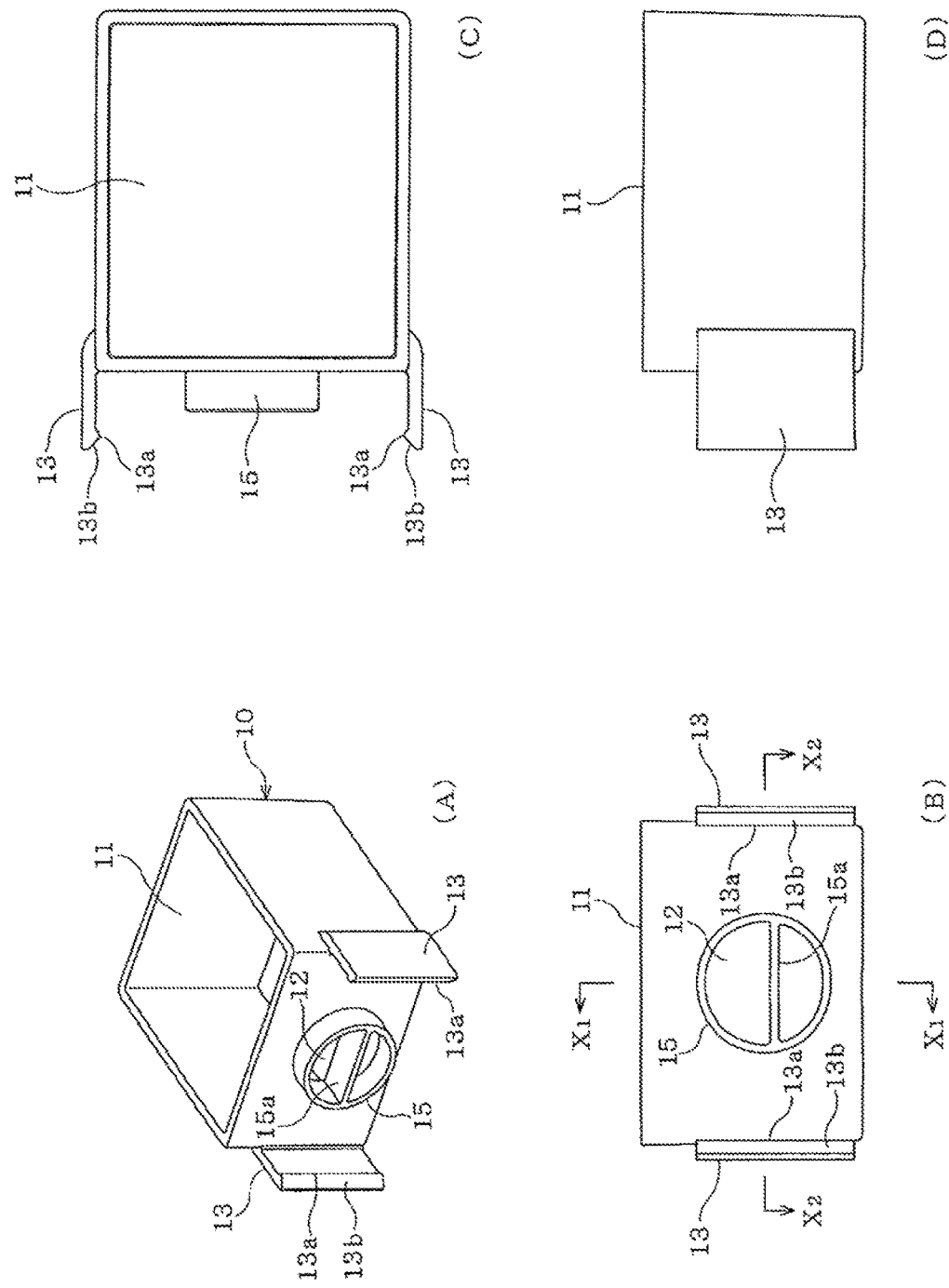

[Fig.3]
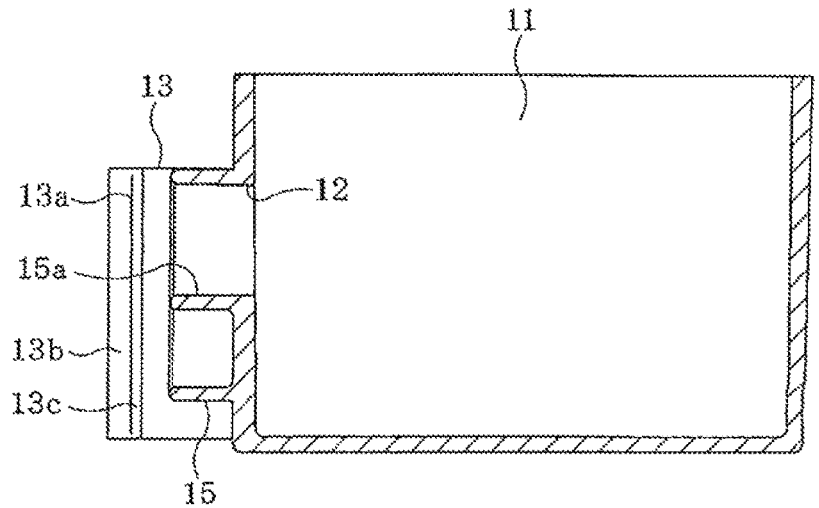
(A)
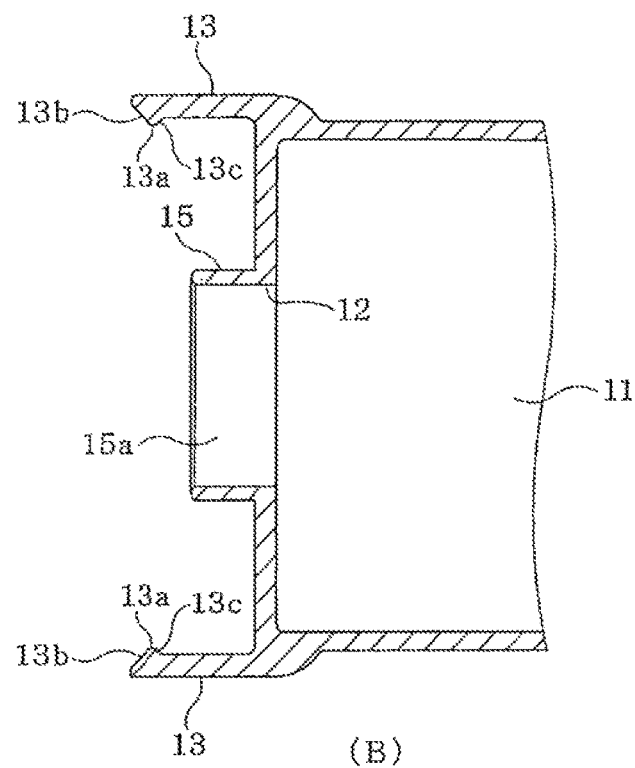
(B)

[Fig.4]
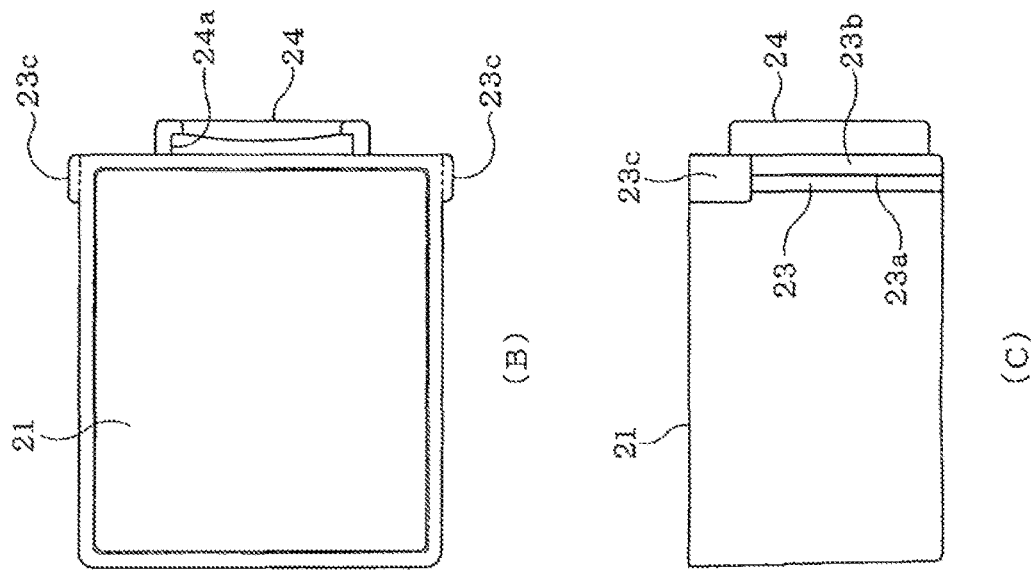
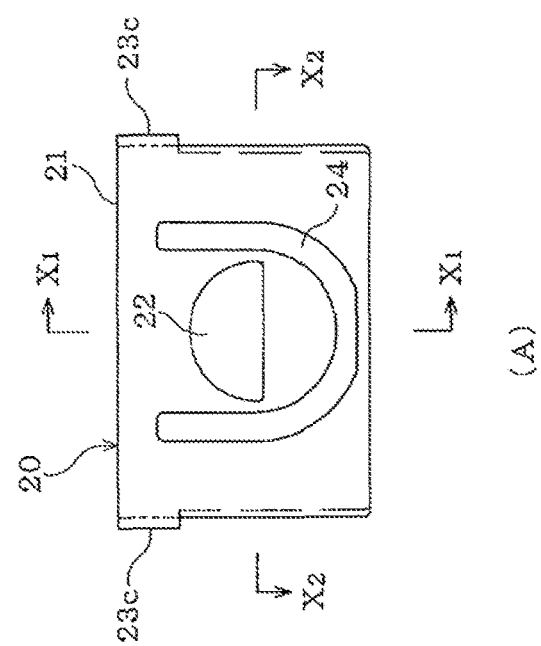

[Fig.5]
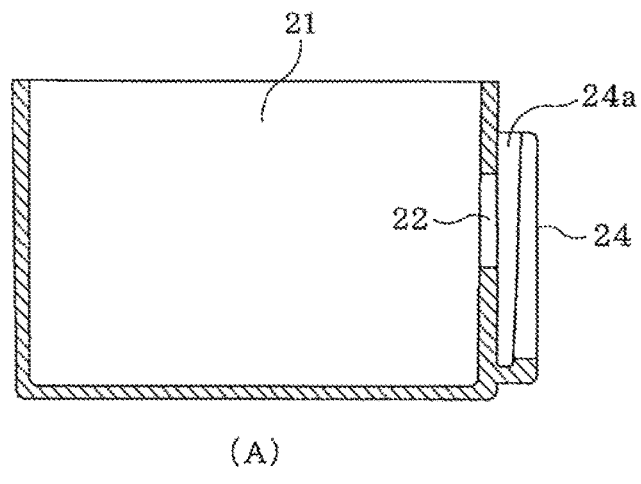
(A)
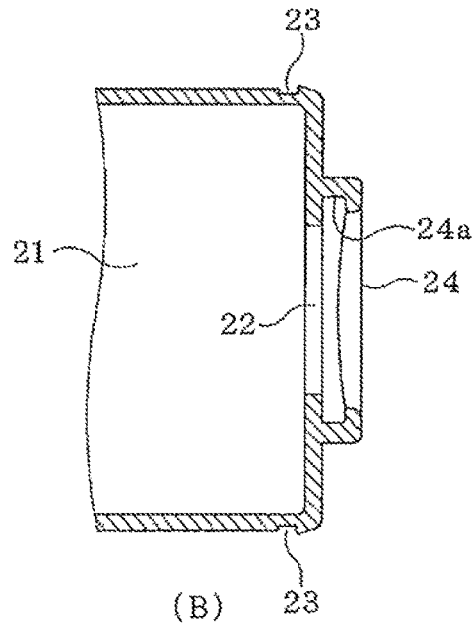
(B)
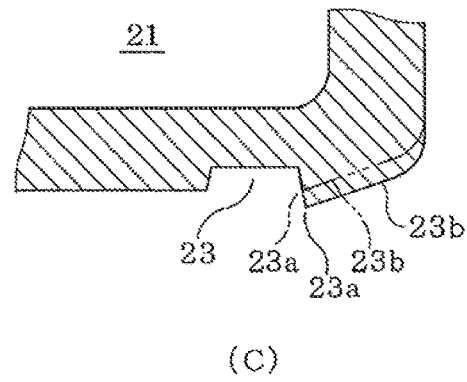
(C)

[Fig.6]
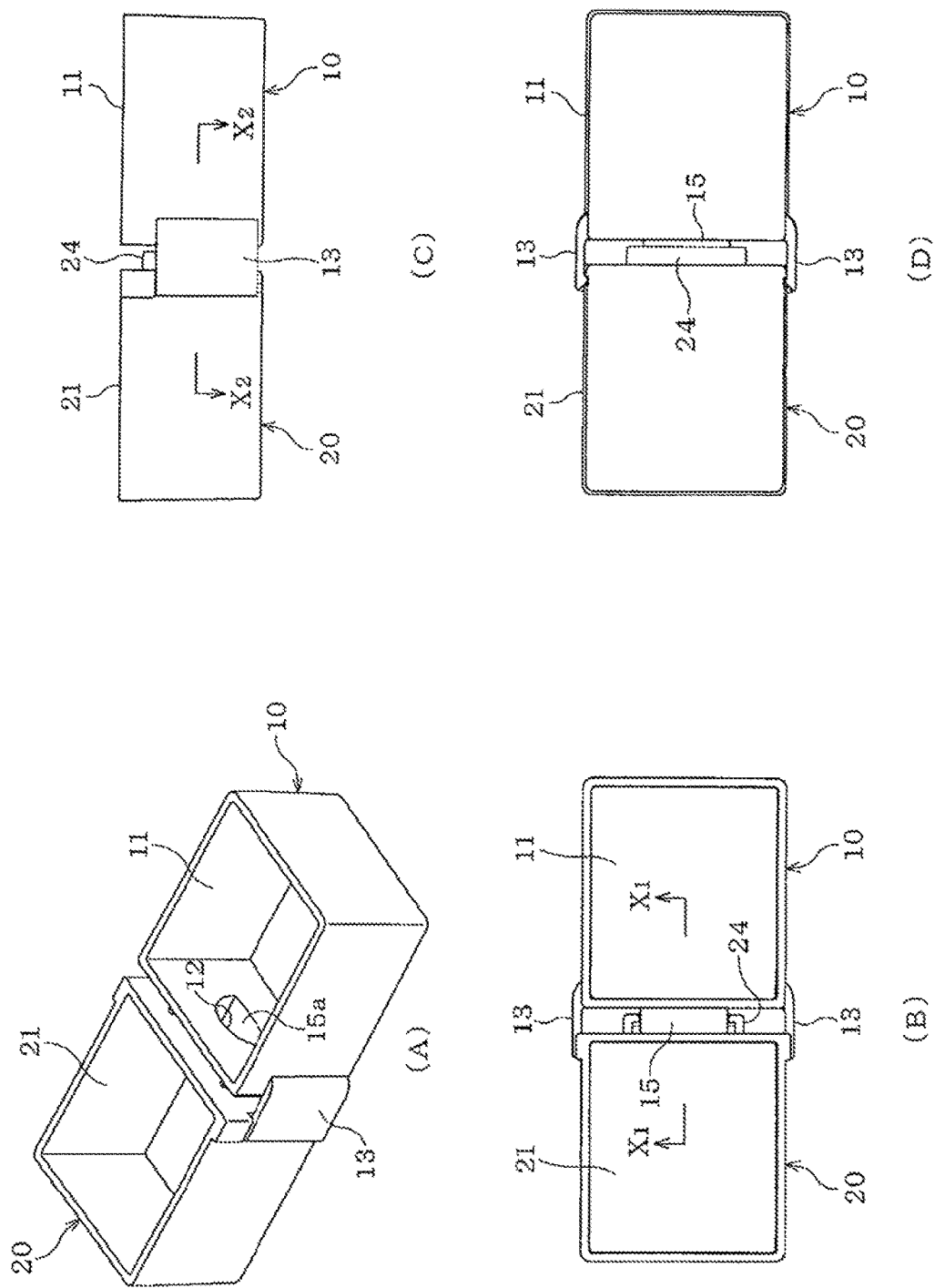

[Fig.7]
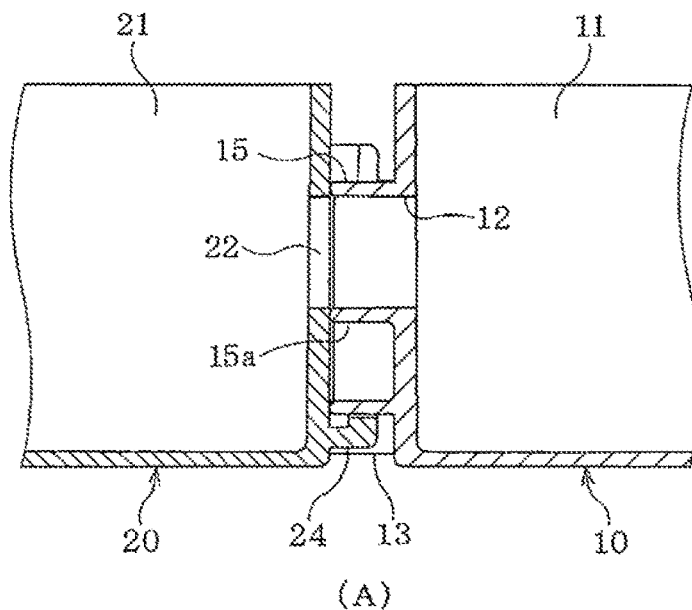
(A)
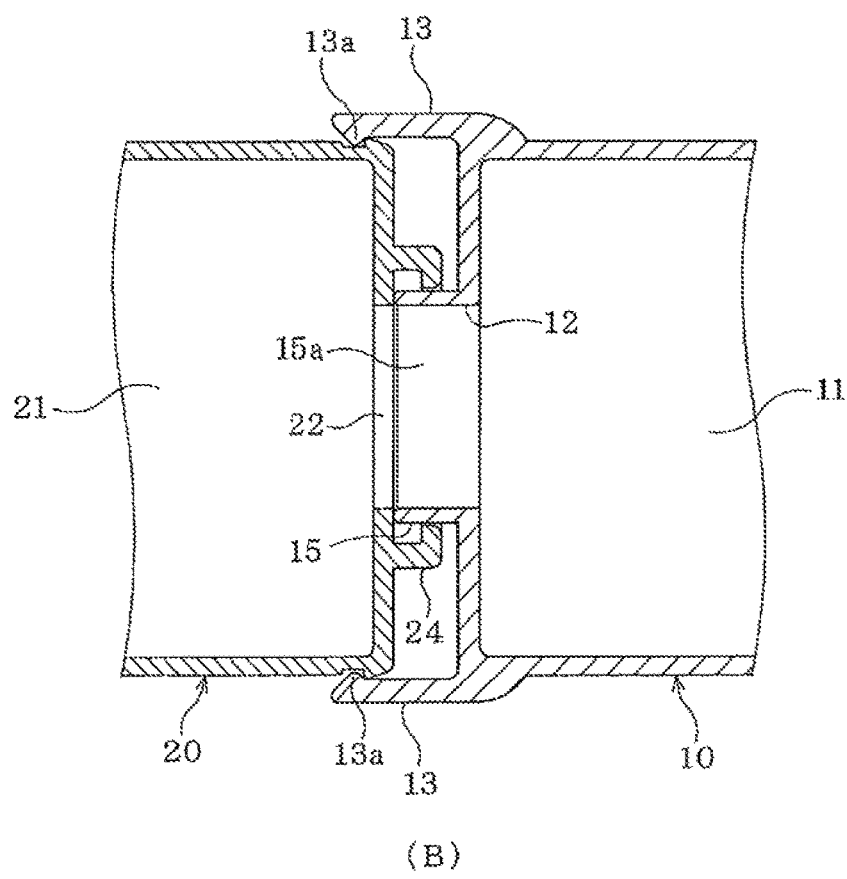
(B)

[Fig.8]
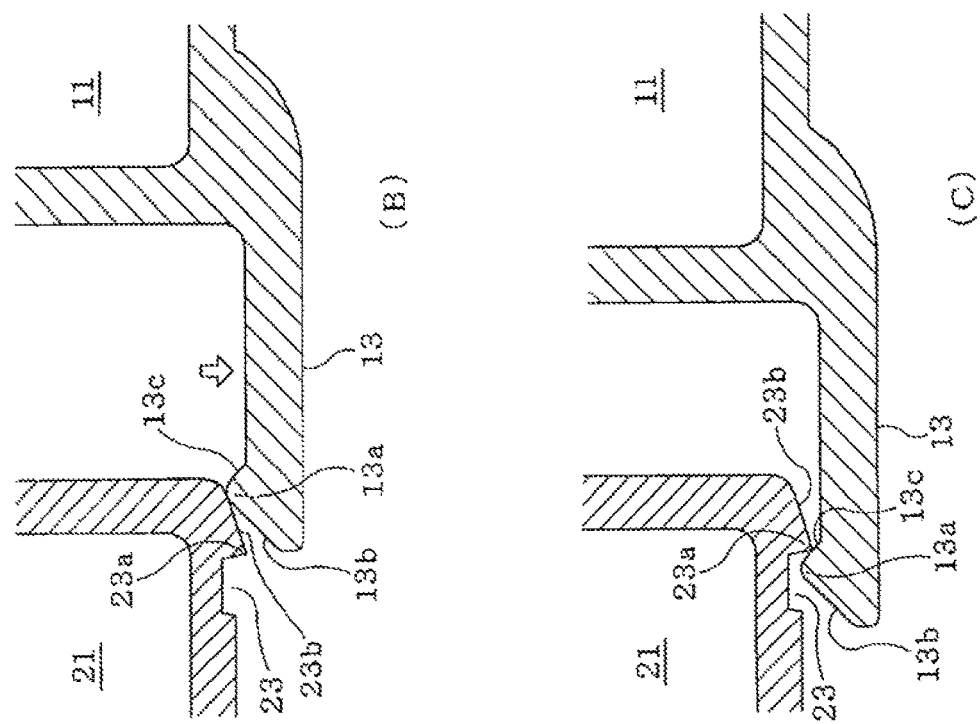
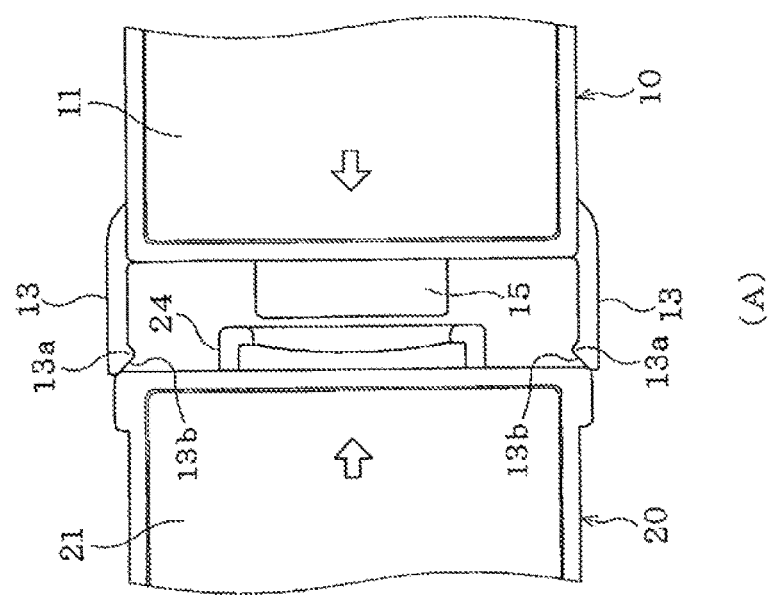

[Fig.9]
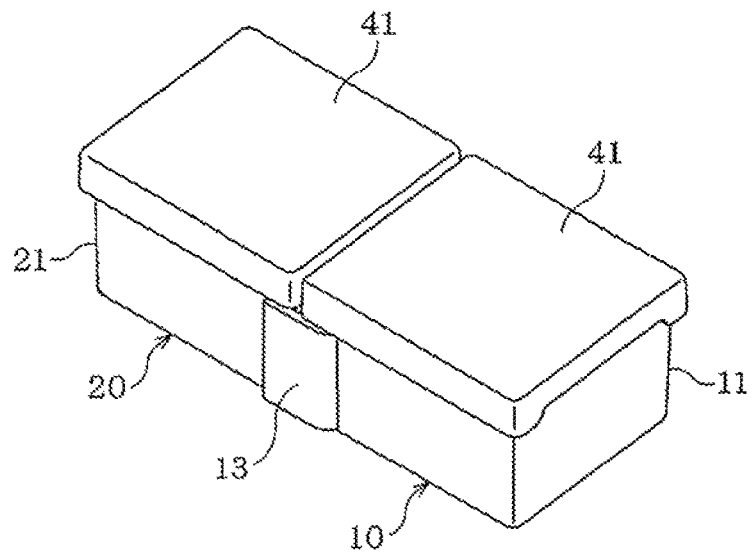
(A)
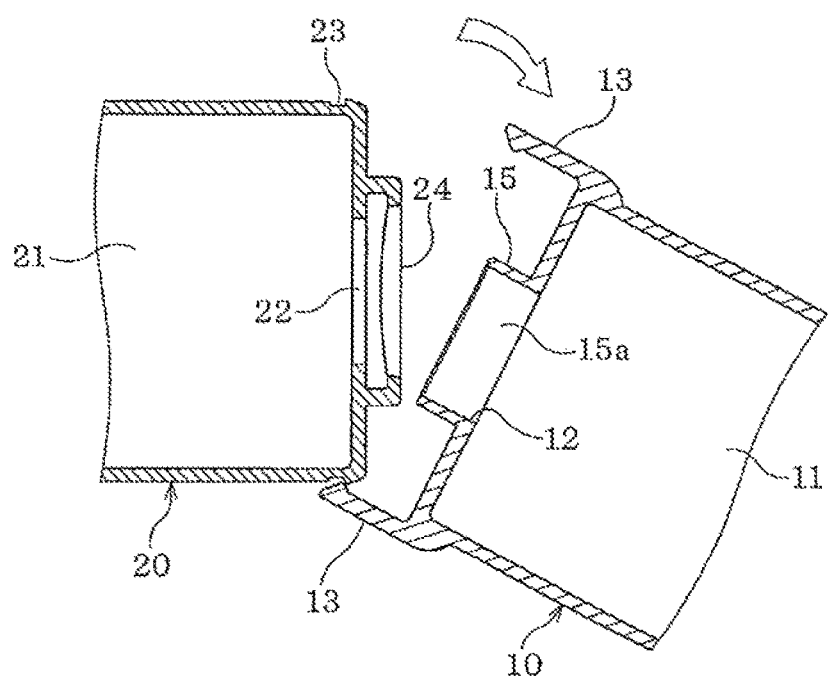
(B)

[Fig.10]
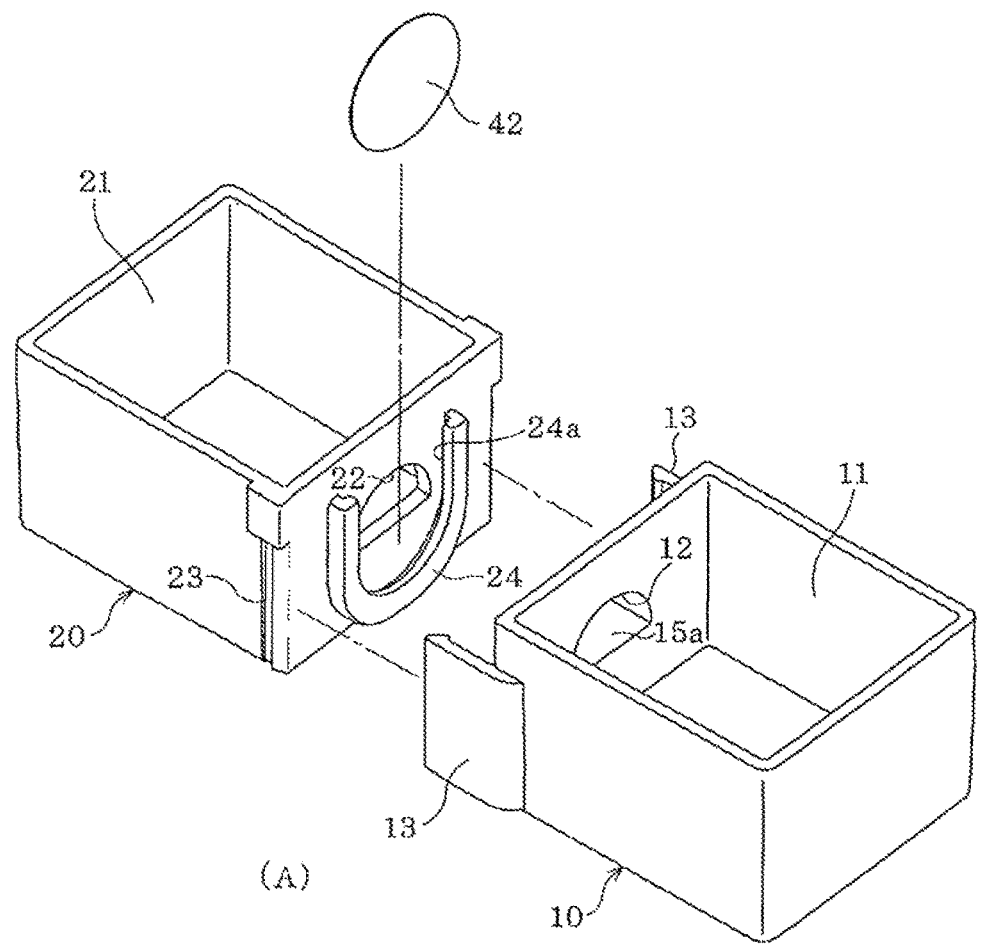
(A)
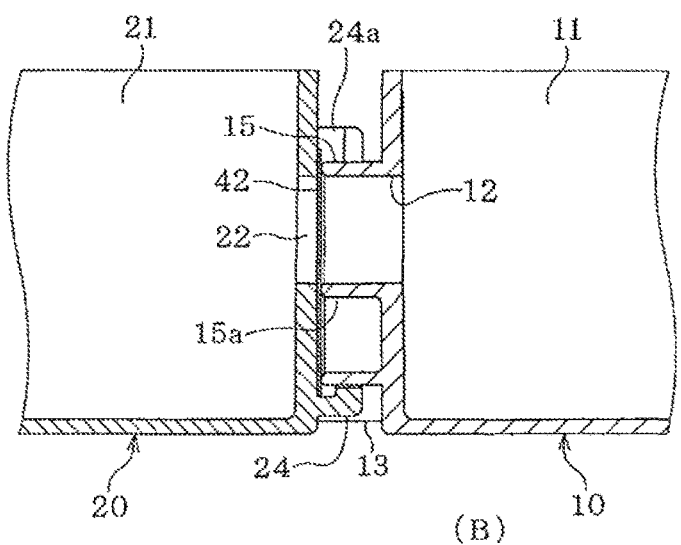
(B)

[Fig.11]
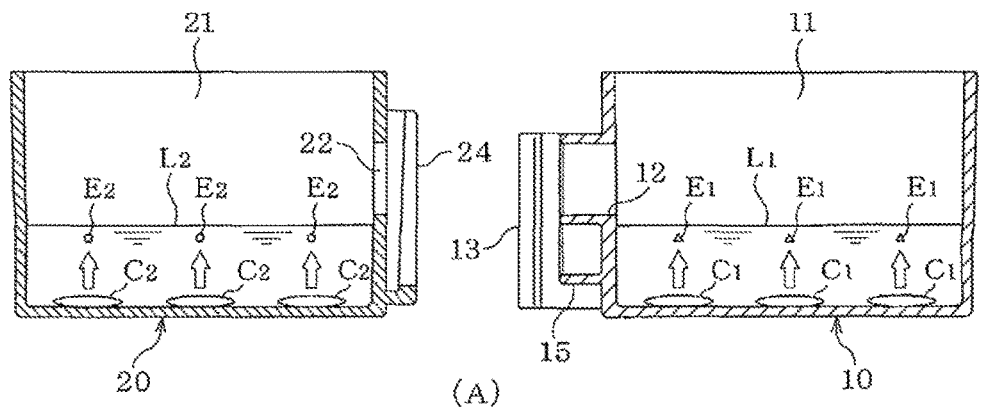
(A)
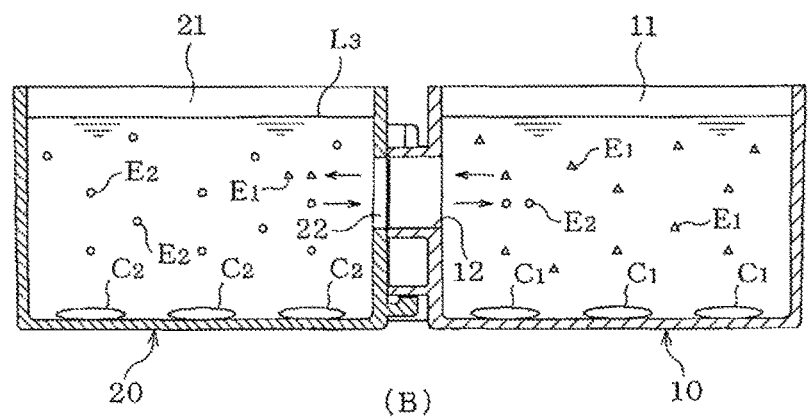
(B)
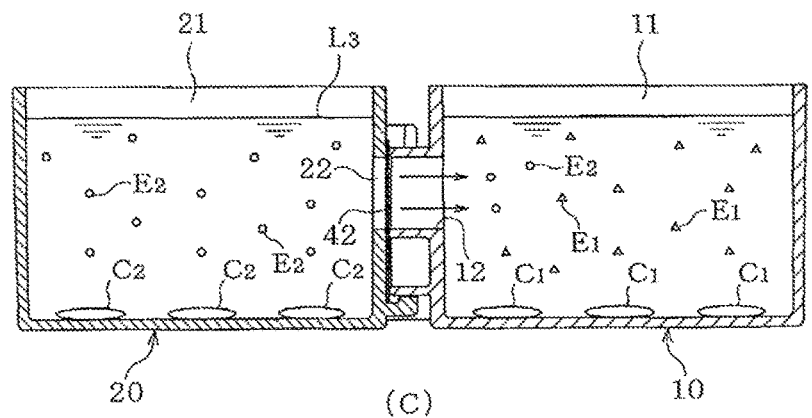
(C)

[Fig.12]
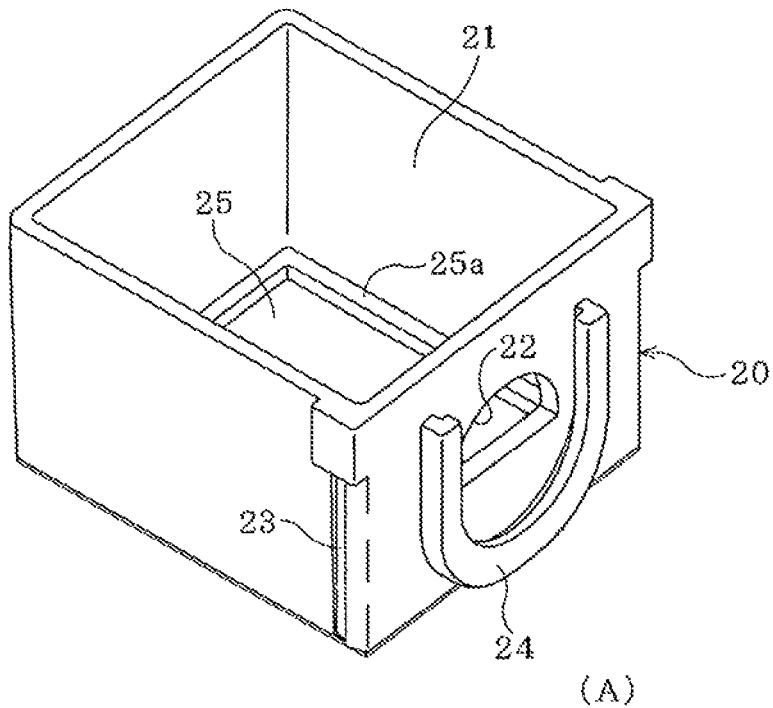
(A)
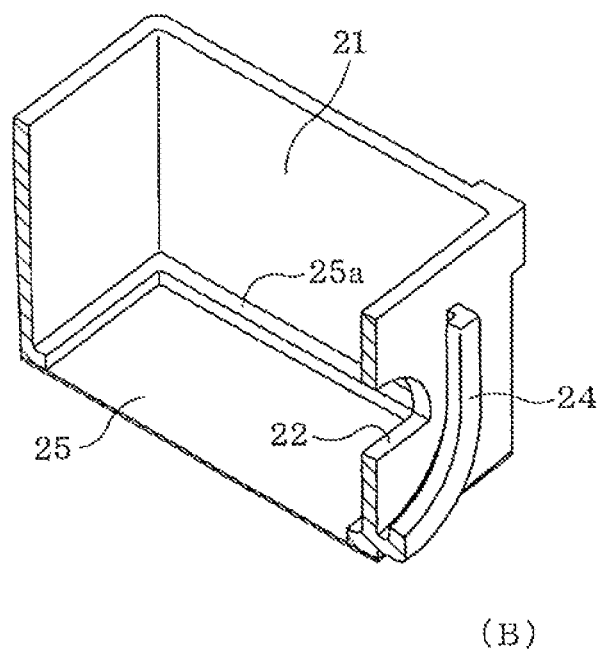
(B)

[Fig.13]
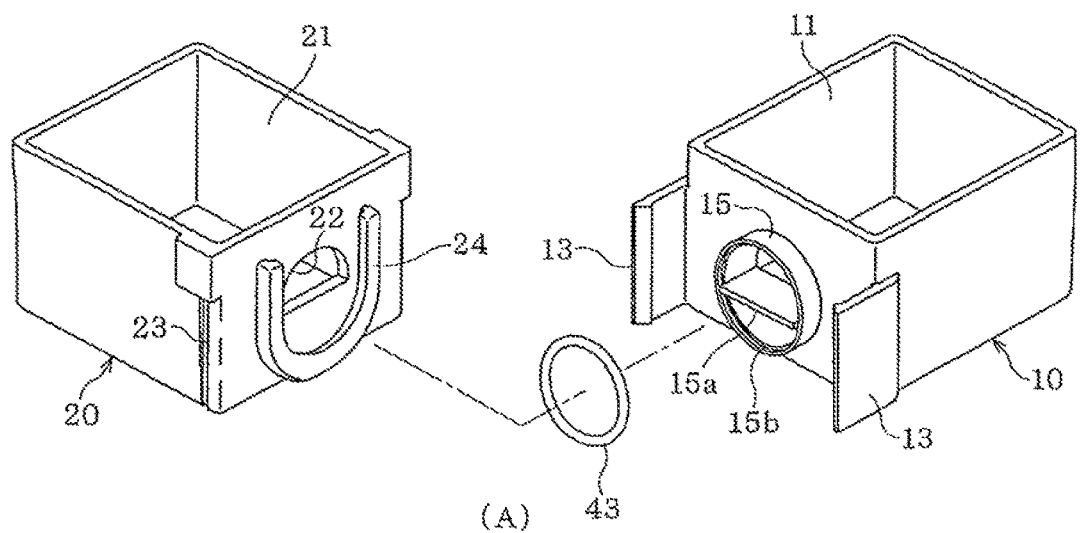
(A)
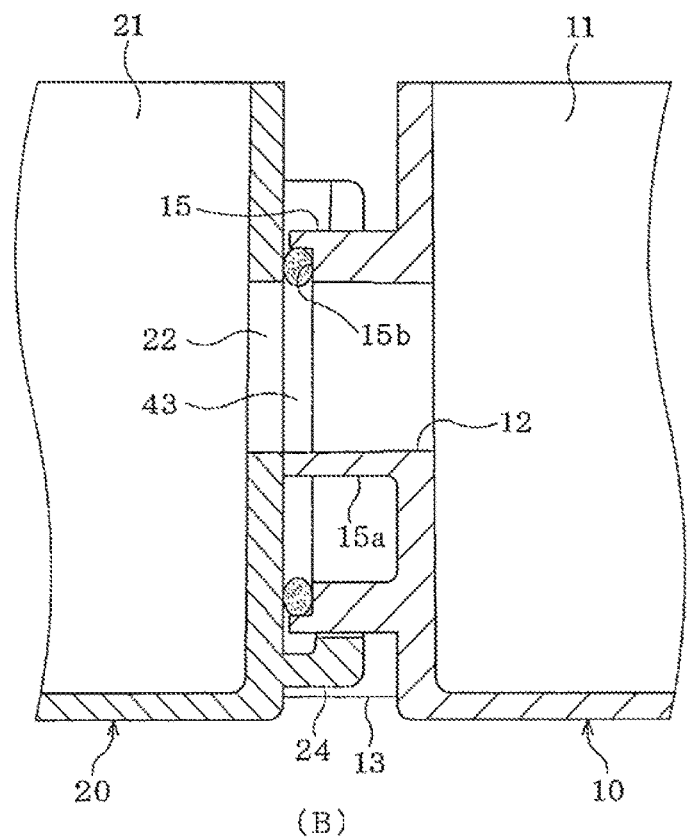
(B)

[Fig.14]
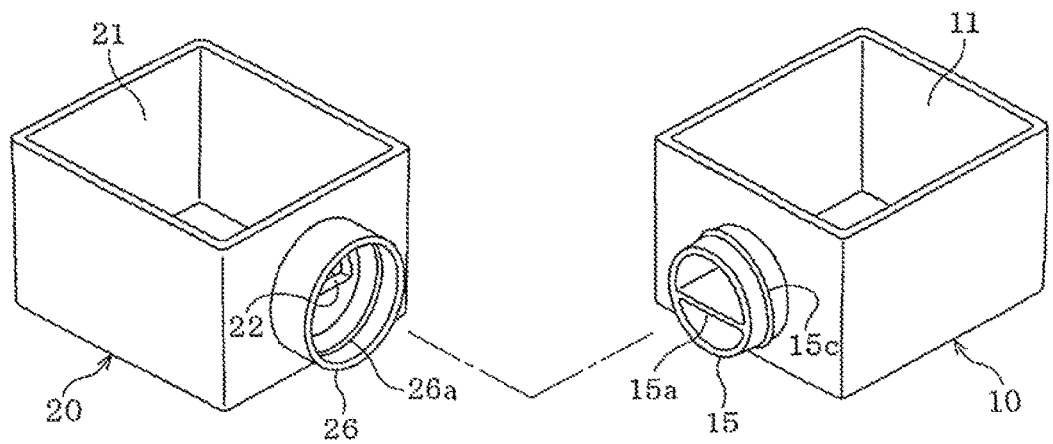
(A)
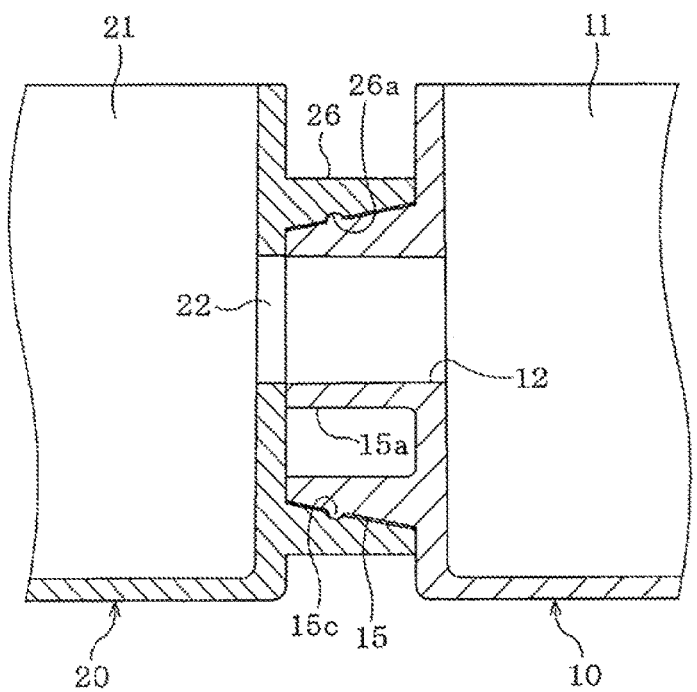
(B)

[Fig.15]
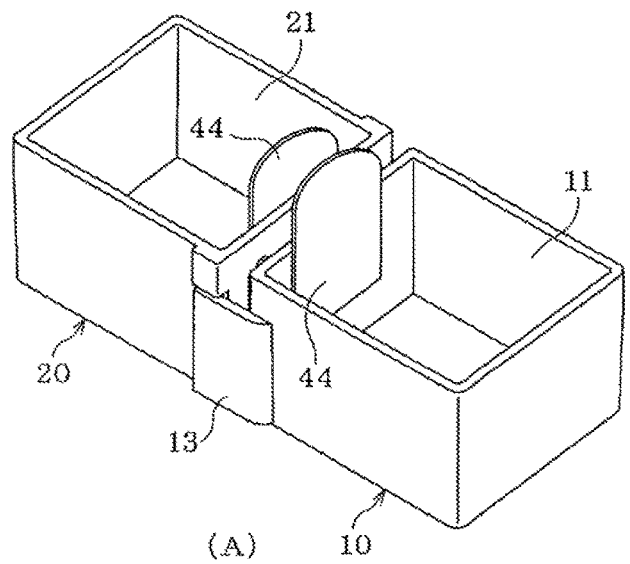
(A)
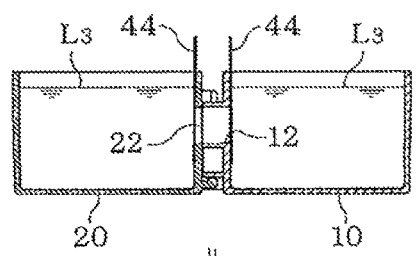 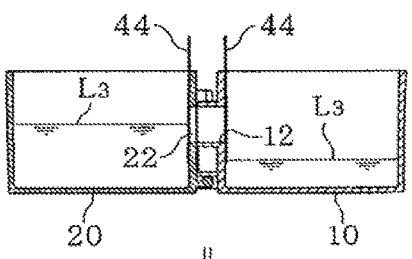
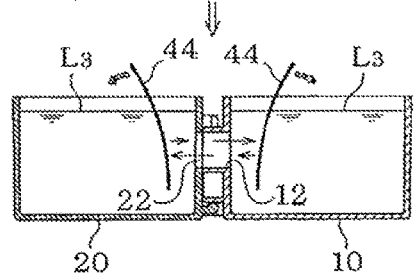 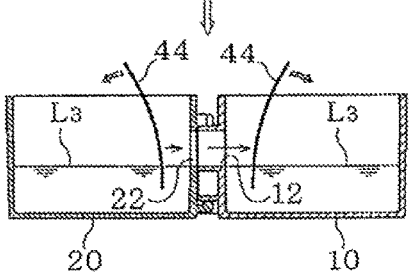
(B) (C)

[Fig.16]
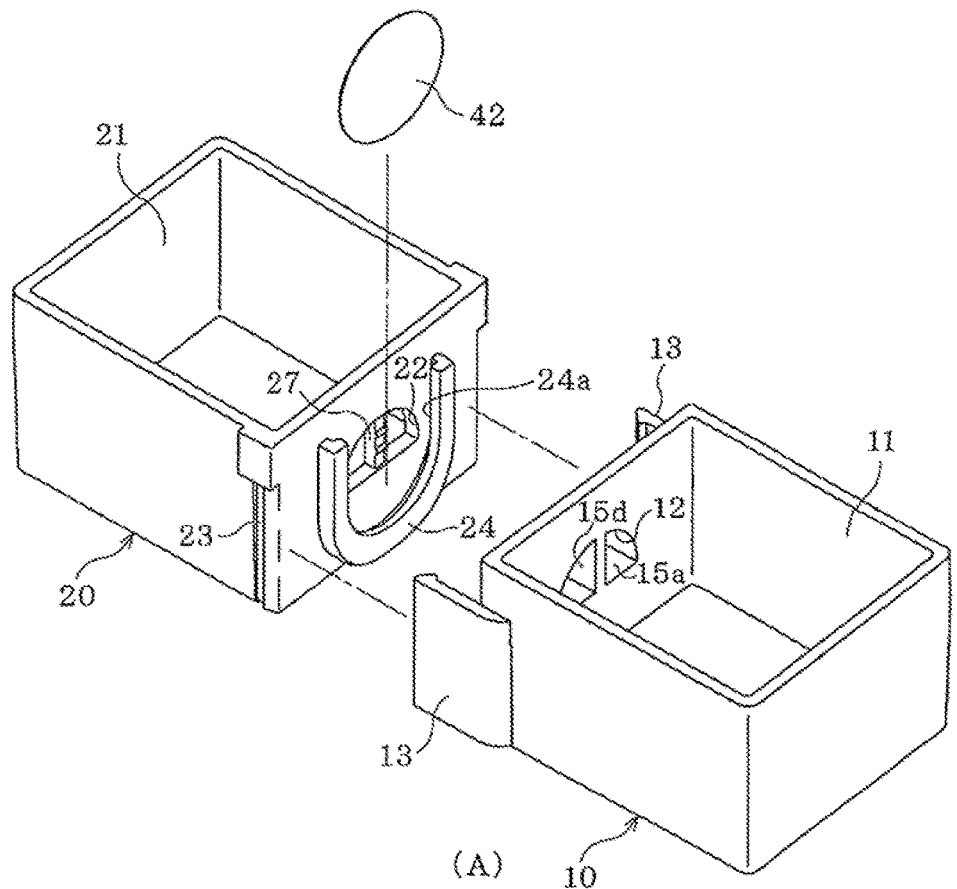
(A)
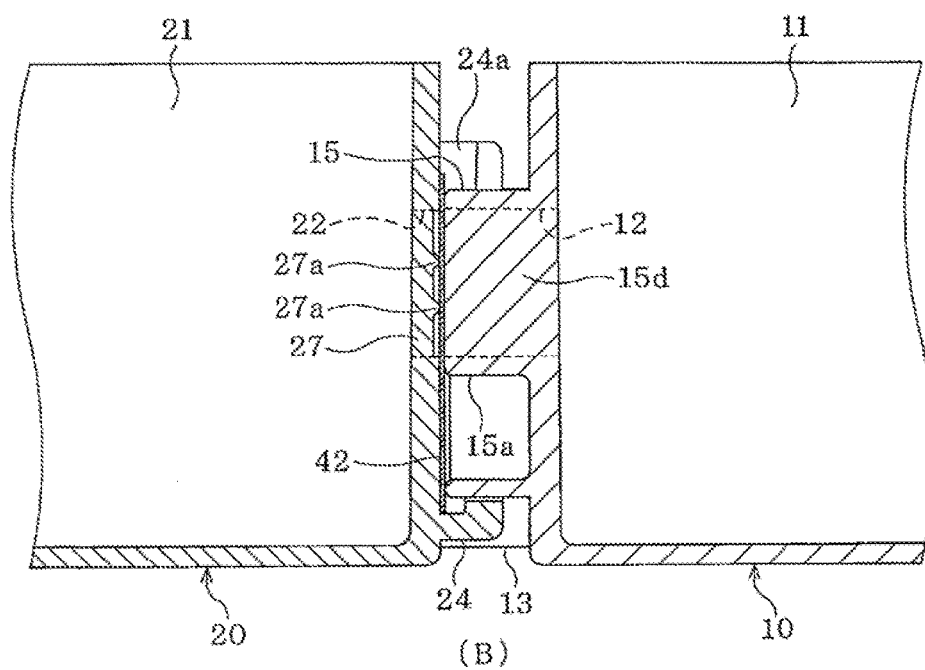
(B)

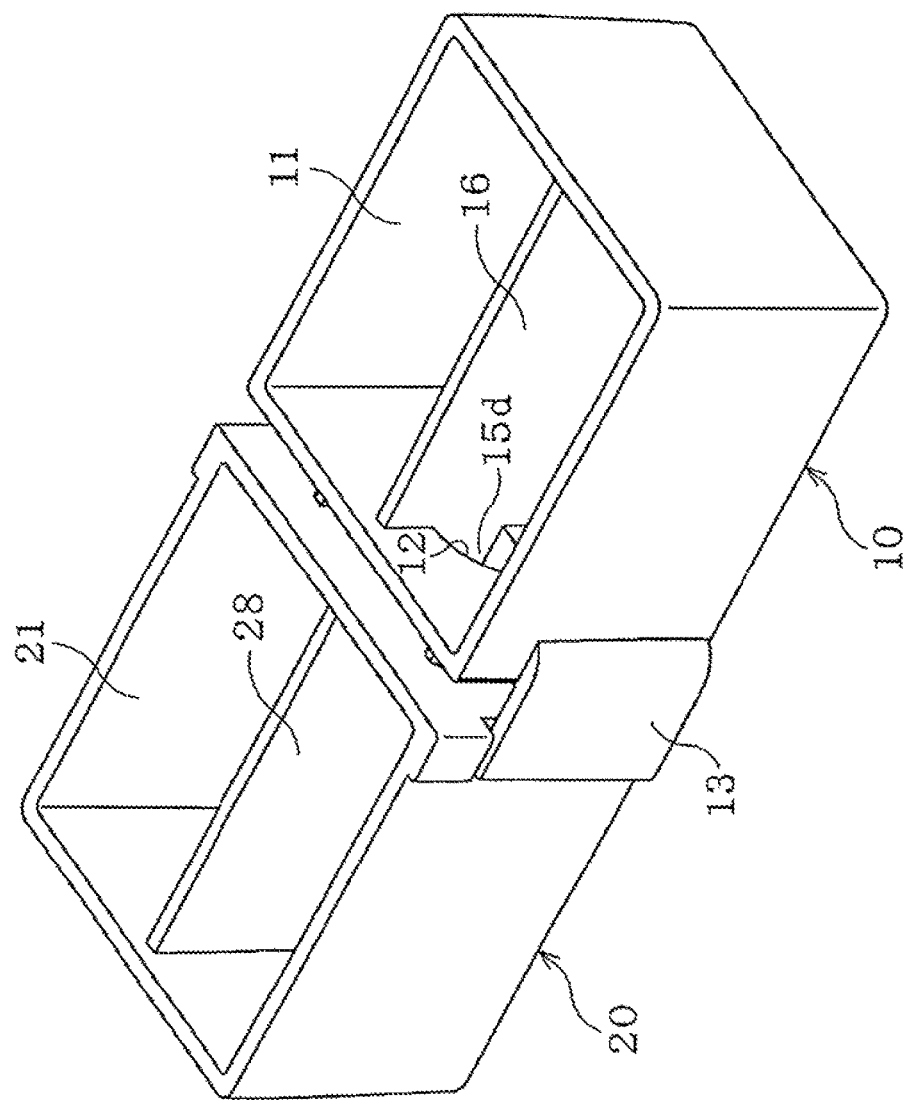
[Fig.17]

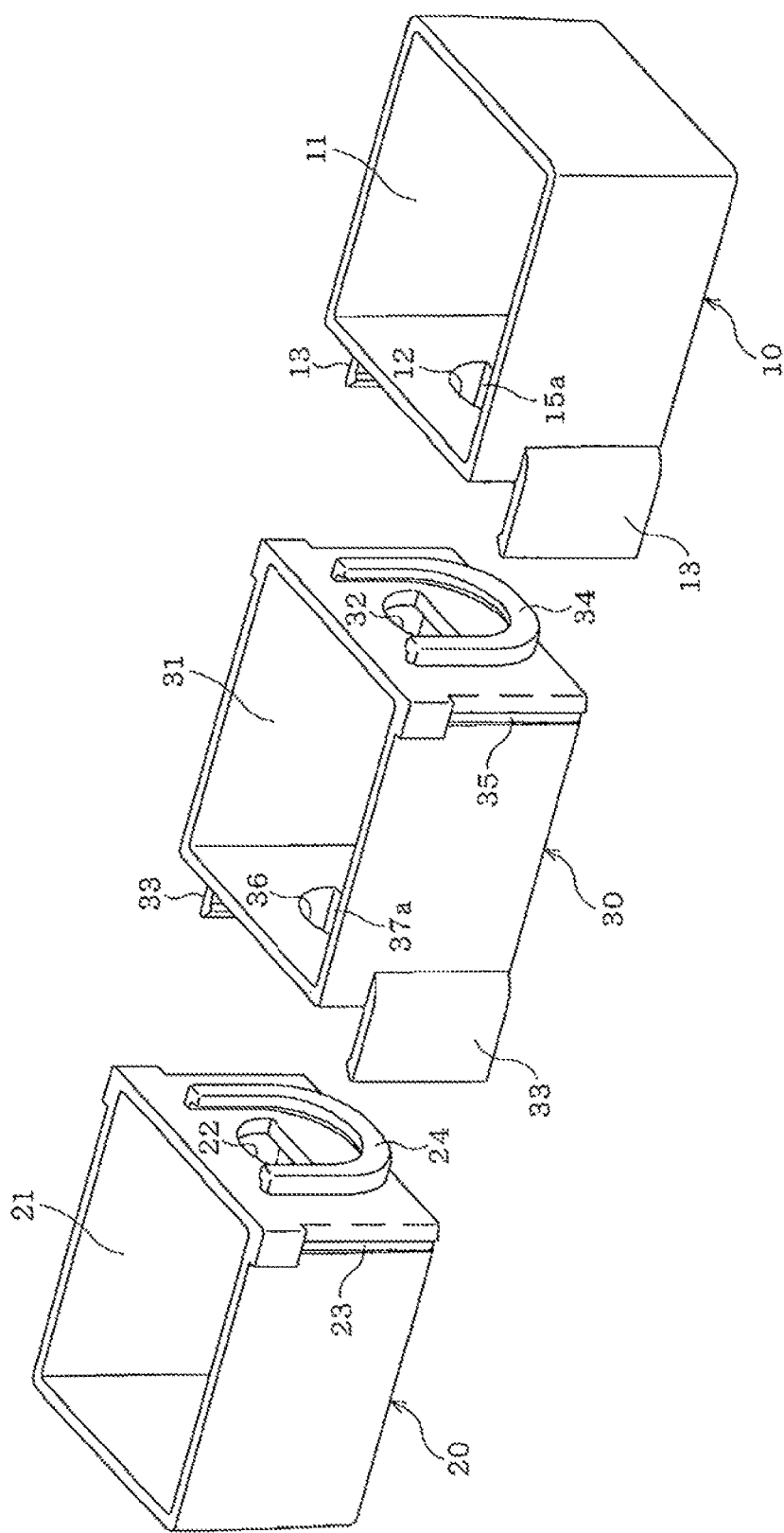
[Fig.18]

[Fig.19]
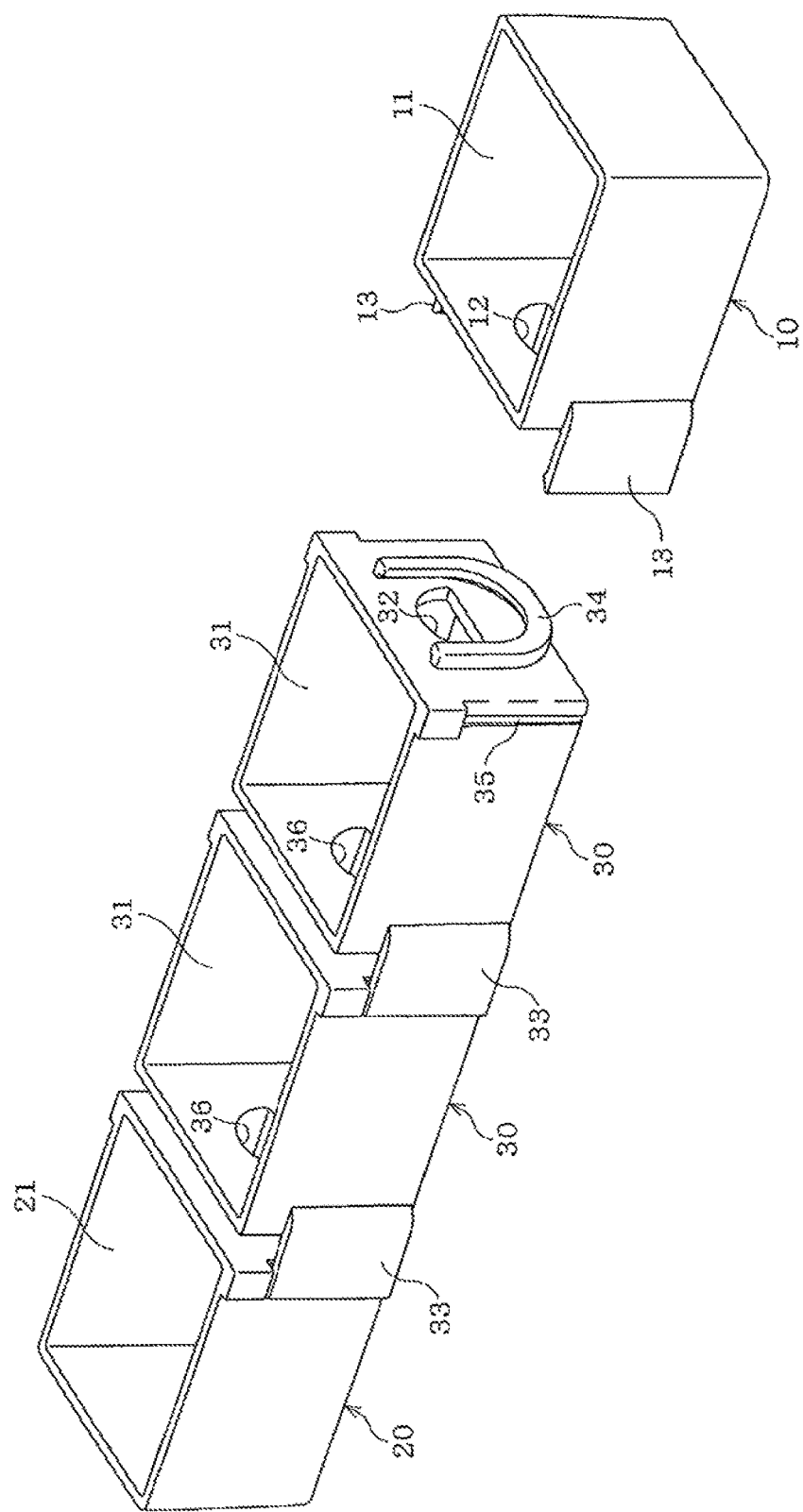

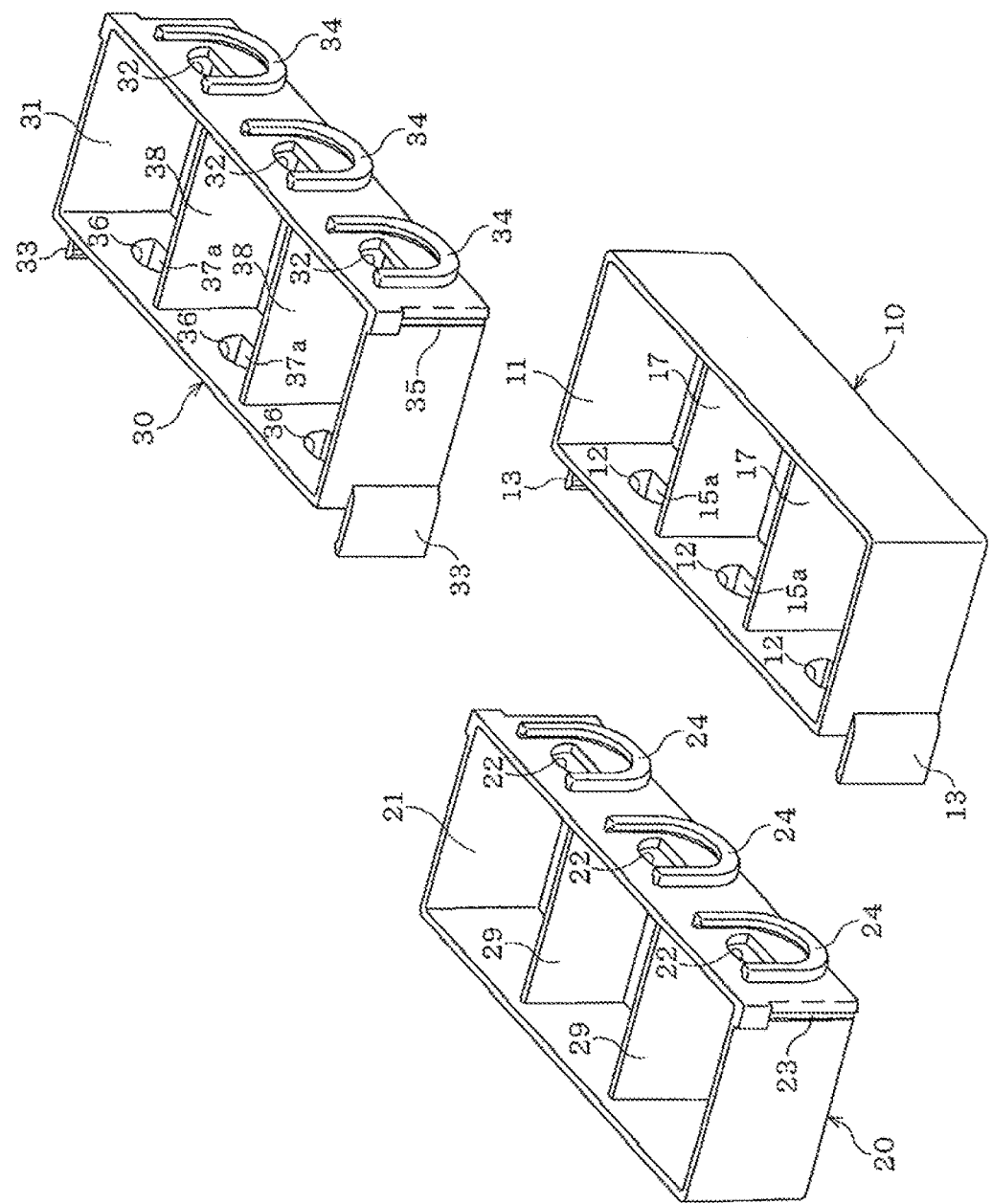
[Fig.20]

[Fig.21]
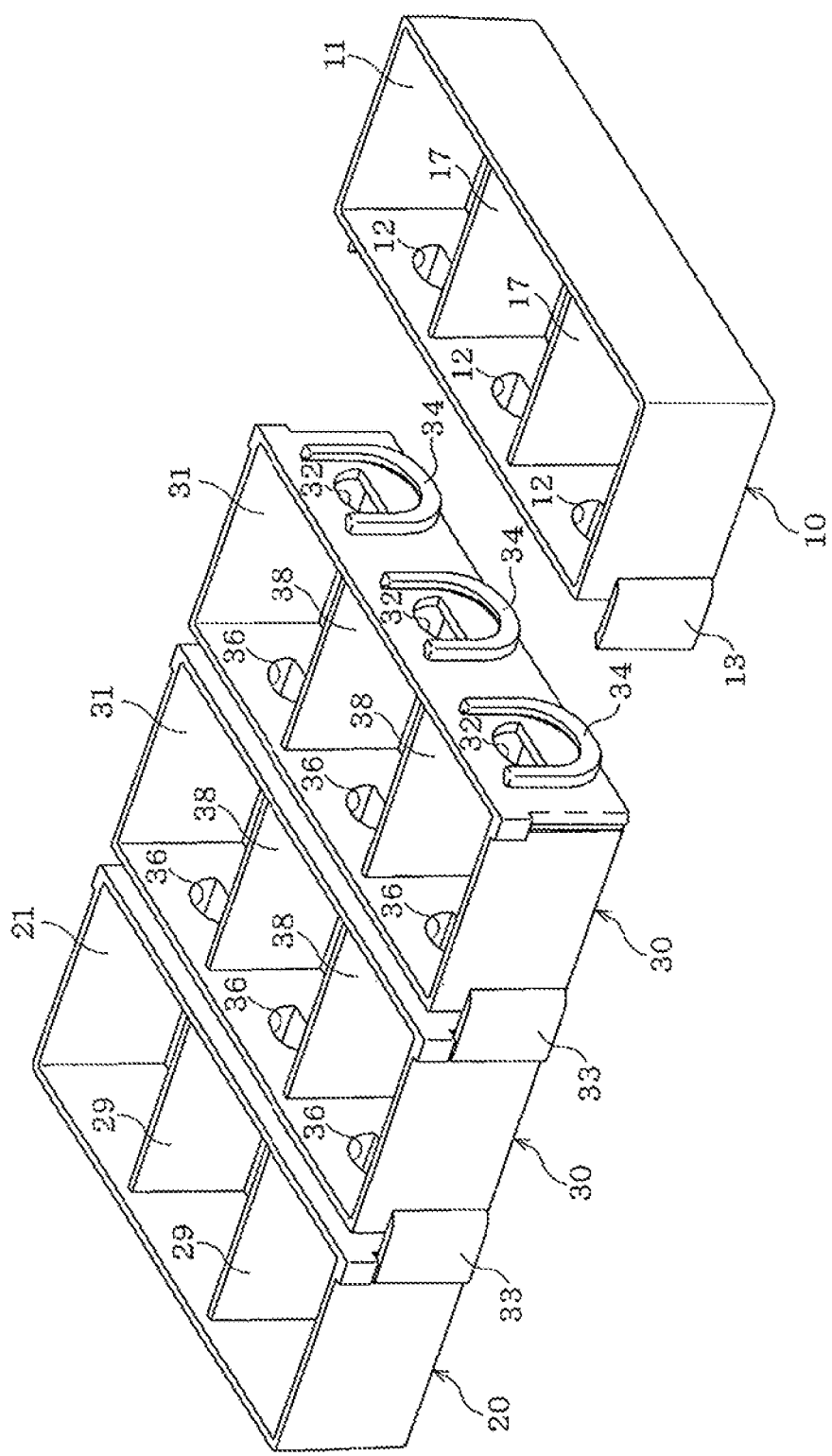

[Fig.22]
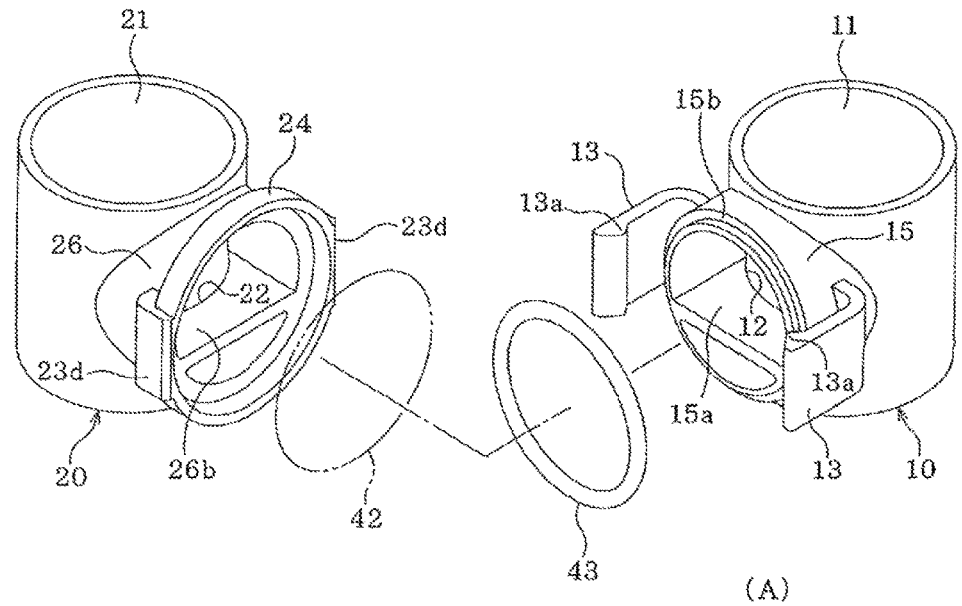
(A)
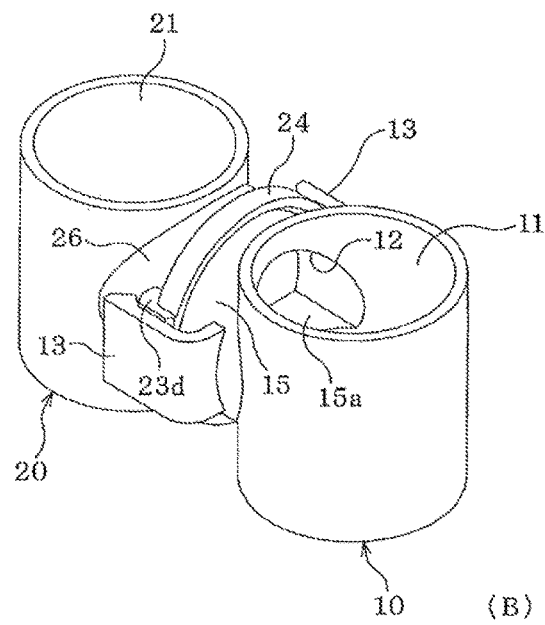
(B)

CULTURE VESSEL

TECHNICAL FIELD

The present invention relates to a culture vessel which is especially useful, for example, for the experimental research on the interaction between cells cultured in an arbitrary environment.

BACKGROUND ART

A culture device capable of co-culturing multiple species of cells, and examining the interaction between these cells has been proposed (Patent Document 1).

The conventional culture device is a so-called multi-well type device in which a plurality of wells (recesses) for cell culture are formed on a common plate-like vessel body, and a high outer wall is provided so as to surround the outer periphery of the vessel body. In culturing specified cells in different wells, a common liquid culture medium is poured inside the outer wall to overflow it from these wells, and the interaction between the cells in the respective wells expressed via the liquid culture can be observed. For example, by culturing cell species derived from various organs such as liver, kidney, heart, spleen, lung, and blood vessel in the different wells, it is possible to simulate the interaction between cell species of these organs in a living body.

PRIOR ART DOCUMENTS

Patent Documents

Patent Document 1: JP 4809799 B1

SUMMERY OF THE INVENTION

Problems to be Solved by the Invention

The conventional technique, however, has the problem that the culture environment for each cell species cannot be set individually because the wells for cell culture are formed on the common vessel body, and the required data cannot be obtained. For example, when a tumor increases as a result of proliferation of cancer cells, angiogenesis is induced because the center part of the tumor is brought into a low-oxygen environment. For studying the secretor factors such as cytokine and exosome involved in induction of angiogenesis, and the behaviors thereof, it is necessary to observe the interaction between cancer cells and normal cells cultured in various culture environments including the low-oxygen environment. Also the conventional technique has a problem that it is substantially unsuited for identification of the secrete factors such as cytokine and exosome because the wells on the common body cannot be separated individually by means of a filter.

In light of these problems in the conventional technique, it is an object of the present invention to provide a culture vessel that is suited not only for observation of the interaction between cells individually cultured in an arbitrary environment, but also for identification of secretor factors, and culture, regeneration, manufacture, observation and the like of targets such as cells, organs, and microorganisms, for example, by combining a first vessel and a second vessel that are connectable to each other.

Solutions to the Problems

For achieving the above object, the feature of the present invention is a culture vessel including a first vessel and a second vessel formed of a transparent thermoplastic material. The first vessel and the second vessel are respectively closed-bottom, open-top vessels having a sideways-facing opening, and the respective openings communicate in a watertight manner when the openings are connected face to face via a connecting mechanism formed on the first vessel and the second vessel.

Each of the openings can be formed into a semicircle with the circular arc upside.

The first vessel may be formed with a cylindrical member outwardly that surrounds the opening. The second vessel may be formed with a guide member for positioning the cylindrical member when the second vessel is connected with the first vessel. In the second vessel, a filter may be retained on the front face of the opening, and the opening may be provided with is supporting rod for supporting the filter.

Respective bottom faces of the first vessel and the second vessel may be formed of a separate transparent plate. In the first vessel and the second vessel, the each of the openings may be closed via a strippable film. In each of the first vessel and the second vessel, the interior together with the opening may be divided into two rooms.

The first vessel and the second vessel can be connected via a third vessel in which a pair of sideways-facing openings are symmetrically provided. In each of the first vessel, the second vessel and the third vessel, the interior can be divided into multiple rooms, and each of the rooms can be provided with the opening.

Effects of the Invention

According to such a feature of the present invention, the first vessel and the second vessel can be independently put in individual environments, and cells can be cultured in respective environments. Meanwhile, in the first vessel and the second vessel, when the respective openings are connected face to face via a connecting mechanism, the openings communicate in a watertight manner. When a common liquid culture medium is poured into the first vessel and the second vessel, the secretory substances from cultured cells in the first vessel and in the second vessel communicate via the liquid culture medium, and hence, by further continuing the culture, it is possible to observe the interaction between the cells cultured in the different environments. The first vessel and the second vessel, formed, for example, of a transparent thermoplastic material such as polystyrene, having subjected to a hydrophilization treatment such as a plasma treatment on the inner surface advantageously facilitate immobilization of targets such as cells, organs and microorganisms, and facilitate the observation. Also, by connecting the first vessel and the second vessel via the filter, the vessels can be suitably used for identification of the secretor factors.

By forming each opening into a semicircle with the circular arc upside, the space between the linear part of the lower part, and the bottom feces of the first vessel and the second vessel can be used as an effective space for use in culture, regeneration, manufacture, observation and the like of the targets. The shape of each opening is not necessarily a perfect semicircle, and may be larger or smaller than a semicircle, and is advantageously larger than a semicircle in the point of increasing the effective opening area.

When the first vessel and the second vessel are connected, the outward cylindrical member surrounding the opening of the first vessel come into abutment around the opening of the second vessel at its tip end to allow communication between the openings in a watertight manner. At this time, the guide member formed in the second vessel can position the tip end of the cylindrical member of the first vessel and set the relative positional relation between the cylindrical member and the opening of the second vessel appropriately. Also, an outward cylindrical member may be formed in the opening of the second vessel, and a guide member for positioning the cylindrical member of the first vessel may be formed in the tip end of the cylindrical member of the second vessel.

The filter retained on the front face of the opening of the second vessel fractionate, for example, the secretory substances that contribute to the interaction between cultured cells in the first vessel and in the second vessel, namely the secretor factors depending on the size, and contributes to identification and analysis thereof. The permeation pore size of the filter can be selected in consideration of, for example, the size of exosome that is estimated to be about 30 to 100 nm in diameter. Also by providing the opening of the second vessel with a supporting rod for supporting the filter, it is possible to retain the filter stably even if the opening is increased.

Forming the bottom faces of the first vessel and the second vessel of a transparent plate is advantageous in microscopic observation of targets through the transparent plate. Since the transparent plate is thin, its light transmission is further excellent, and the microscopic observation at high magnification is facilitated.

By closing the openings of the first vessel and the second vessel via the strippable film, it is possible to make the liquid culture medium in the first vessel and the liquid culture medium in the second vessel communicate at once by stripping and removing the film, and it is possible to eliminate the opportunity of malfunction caused by disturbance on the target, and dilution of the secretor factor occurring in the case of communicating live opening by additionally pouring the liquid culture medium.

Dividing the interior of the first vessel and the second vessel into two rooms allows effective use for the comparison test and screening of normal cells and cancer cells cultured in the same condition in different rooms.

When the first vessel and the second vessel are connected with the third vessel in which a pair of sideways-facing openings are symmetrically provided, interposed therebetween, it is possible to observe the interaction between cultured cells of three or more species, for example. The third vessel can be interposed between the first vessel and the second vessel while one or arbitrary number of the third vessels are connected in series. The openings of the third vessel are adapted to the respective openings of the first vessel and the second vessel. The third vessel is basically formed of the same material into the same shape and size as the first vessel and the second vessel, and forms a connecting mechanism that is combined with the connecting mechanism of the first vessel and the second vessel.

When the interior of each of the first vessel, the second vessel and the third vessel is divided into plural rooms, it is possible to accommodate different species of cells in the different rooms, and culture them in the same conditions, for example, so that it is more effective for the purpose of comparative test and screening. At this time, since the first vessel, the second vessel and the third vessel are provided with the respective openings for each room, it is possible to efficiently conduct a comparison test based on the secretory factor from the cultured cells by attaching an appropriate filter to each opening of each room.

BRIEF DESCRIPTION OF THE DRAWINGS

FIG. 1 is an exploded perspective view of the overall structure.

FIG. 2 is an explanatory diagram of the structure of a first vessel.

FIG. 3 is an enlarged explanatory diagram of the essential part in FIG. 2.

FIG. 4 is an explanatory diagram of the structure of a second vessel.

FIG. 5 is an enlarged explanatory diagram of the essential part in FIG. 4.

FIG. 6 is an explanatory diagram of the connected state.

FIG. 7 is an enlarged explanatory diagram of the essential part in FIG. 6.

FIG. 8 is an explanatory diagram of the connecting operation (1).

FIG. 9 is an explanatory diagram of the connecting operation (2).

FIG. 10 is an explanatory diagram of the connecting operation (3).

FIG. 11 is a schematic diagram of the use condition.

FIG. 12 is an explanatory diagram of the structure (1) showing other embodiment.

FIG. 13 is an explanatory diagram of the structure (2) showing other embodiment.

FIG. 14 is an explanatory diagram of the structure (3) showing other embodiment.

FIG. 15 is an explanatory diagram of the structure (4) showing other embodiment.

FIG. 16 is an explanatory diagram of the structure (5) showing other embodiment.

FIG. 17 is a perspective view of the connected state showing other embodiment.

FIG. 18 is an exploded perspective view (1) showing other embodiment.

FIG. 19 is a perspective view of the connected state in FIG. 18.

FIG. 20 is an exploded perspective view (2) showing other embodiment.

FIG. 21 is a perspective view of the connected state in FIG. 20.

FIG. 22 is an explanatory diagram of the structure (6) showing other embodiment.

MODE FOE CARRYING OUT THE INVENTION

Hereinafter, embodiments of the present invention will be described by referring to the drawings.

A culture vessel includes a first vessel 10 and a second vessel 20 (FIG. 1). The following description will be made while mainly taking the use for cell culture as an example.

The first vessel 10 is a closed-bottom, open-top vessel (FIG. 1 and FIG. 2), and has a sideways-facing opening 12 formed on one end surface in the longitudinal direction of a vessel body 11 with the rectangular box shape, and a pair of engagement parts 13, 13 protruding in the extended directions of the right and left lateral walls of the end surface on the side of the opening 12. FIG. 2(A) is a perspective view of the first vessel 10, and FIGS. 2(B), 2(C), and 2(D) are a front view, a top view, and a lateral view on the side of the opening 12, respectively.

The opening 12 is formed into a semicircle with the circular arc upside. Around the opening 12, a cylindrical member 15 surrounding the opening 12 is outwardly formed. The cylindrical member 15 is formed into a cylindrical shape with the inside diameter the same as the diameter of the opening 12, and inside the cylindrical member 15, a horizontal partition plate 15a is attached along the linear portion of the lower side of the opening 12. However, the lower half part of the cylindrical member 15 below the partition plate 15a is closed by the end surface of the vessel body 11 on which the opening 12 and the cylindrical member 15 are formed (FIG. 3(A)). FIG. 3(A) and FIG. 3(B) are enlarged section views viewed in the directions of arrowed lines $X_1$-$X_1$, and $X_2$-$X_2$ in FIG. 2(B), respectively.

The engagement parts 13, 13 are formed on the right and the left lateral walls of the vessel body 11 protrudingly in such a manner that they hold the cylindrical member 15 therebetween (FIG. 2 and FIG. 3). Each engagement part 13 has a height extending from near the bottom face of the vessel body 11 to near the uppermost position of the cylindrical member 15, and has the protruding length that is sufficiently longer than the length of the cylindrical member 15. In the tip end of each engagement part 13, a conical engagement rib 13a is inwardly formed via a front and a back inclined surfaces 13b, 13c.

The second vessel 20 is a closed-bottom, open-top vessel (FIG. 1 and FIG. 4), and has a sideways-facing opening 22 formed on one end surface in the longitudinal direction of a vessel body 21 with the rectangular box shape, and a pair of vertically-disposed engagement grooves 23, 23 are formed in the positions closer to the end surface of the opening 22 side on the right and the left lateral walls. FIG. 4(A) is a front view of the opening 22 side of the second vessel 20, and FIG. 4(B) and FIG. 4(C) are a top view and a lateral view, respectively.

The vessel body 21 is formed to have the same size as the vessel body 11 of the first vessel 10. The opening 22 is formed to have the same shape and the same size as the opening 12 to correspond to the opening 12 of the first vessel 10. On the end surface in which the opening 22 is formed, an open-top U-shaped guide member 24 is formed from both the right and the left sides to below the opening 22. The upper end of the guide member 24 extends sufficiently higher than the opening 22, and both the interval of upper part, and the radius of curvature of the inside the arcuate portion of the lower part of the guide member 24 are adapted to the outer diameter of the cylindrical member 15 of the first vessel 10.

The guide member 24 is formed inwardly to have an L-shaped section to give a pocket 24a between the guide member 24 and the end surface of the vessel body 21 (FIG. 4(B)). The pocket 24a is formed along the full length of the guide member 24, and narrows linearly downward from the upper end of the guide member 24 (FIG. 5(A)), and smoothly narrows from the right and left end parts to the center part in the arc part of the lower part of the guide member 24 (FIG. 5(B)). FIG. 5(A) and FIG. 5(B) are enlarged section views viewed in the directions of arrowed lines $X_1$-$X_1$, and $X_2$-$X_2$ in FIG. 4(A), respectively and FIG. 5(C) is an enlarged view of the essential part in FIG. 5(B).

The engagement grooves 23, 23 correspond to the engagement parts 13, 13 of the first vessel 10 (FIG. 1, FIG. 5(B) and FIG. 5(C)). Each engagement groove 23 extends from the bottom face of the vessel body 21 to the height corresponding to the upper edge of the engagement part 13. Each engagement groove 23 is formed to have a section in the shape of a unsymmetrical trapezoid that is higher on the side of the end surface in which the opening 22 is formed, and between the engagement groove 23 and the end surface on the side of the opening 22, an apex 23a and an inclined surface 23b are formed. It is to be noted that the section shape of each engagement groove 23 may be a symmetrical trapezoid in which the apex 23a is not high (the two-dot chain line in FIG. 5(C)). Also a vertically long rectangular protrusion 23c that defines the upper end of each engagement groove 28 may be deleted (each two-dot chain line in FIG. 4(A) and FIG. 4(B)).

The first vessel 10 and the second vessel 20 can be detachably connected in such a manner that the respective openings 12 and the openings 22 face each other with the engagement parts 13, 13 of the first vessel 10 and the engagement grooves 23, 23 of the second vessel 20 interposed therebetween (FIG. 6 and FIG. 7). That is, the engagement parts 13, 13 and the engagement grooves 23, 23 serve as a connecting mechanism for connecting the first vessel 10 and the second vessel 20. By connecting the first vessel 10 and the second vessel 20, it is possible to make the tip end of the cylindrical member 15 of the first vessel 10 abut around the opening 22 of the second vessel 20 together with the partition plate 15a, to thereby make the opening 12 and the opening 22 communicate in a watertight manner. FIG. 6(A) is a perspective view of the first vessel 10 and the second vessel 20 in the connected state, and FIGS. 6(B), 6(C), and 6(D) are a top view, a lateral view and a bottom view, respectively. FIG. 7(A) and FIG. 7(B) are enlarged section views viewed in the directions of arrowed lines $X_1$-$X_1$ in FIG. 6(B), and $X_2$-$X_2$ in FIG. 6(C), respectively.

For connecting the first vessel 10 and the second vessel 20, the cylindrical member 15 and the guide member 24 are brought into facing each other on a common plane (not illustrated) (FIG. 8(A)), and a force is applied in the direction of making the first vessel 10 and the second vessel 20 approach each other (the direction of the arrow in FIG. 8(A)). At this time, the engagement parts 13, 13 engage the right and the left corner parts of the vessel body 21 via the inclined surfaces 13b, 13b in the tip end. Then the first vessel 10 and the second vessel 20 are caused to approach each other linearly as they are, and the engagement rib 13a in the tip end of each engagement part 13 runs onto the inclined surface 23b and advances (FIG. 8(B)), and each engagement part 13 elastically deforms outwardly (the direction of the arrow in FIG. 8(B)).

Therefore, as each engagement part 13 further advances and the engagement rib 13a runs over the apex 23a of the engagement groove 23 (FIG. 8(C)), the engagement rib 13a drops into the engagement groove 23, and the apex 23a hangs in the midway of the inclined surface 13c behind the engagement rib 13a and stops. At this time, the cylindrical member 15 is correctly positioned via the guide member 24 (FIG. 7), and the tip end of the cylindrical member 15 abuts around the opening 22, and thus the limit of approach between the first vessel 10 and the second vessel 20 is defined. Therefore, the first vessel 10 and the second vessel 20 receive the force in the direction of approaching each other by the elastic restoring force of each engagement part 13 by engagement of the apex 23a in the midway of the inclined surface 13c, so that there is no fear that sealing of the tip end of the cylindrical member 15 is broken.

The first vessel 10 and the second vessel 20 connected in this manner can be closed on the tops of the vessel body 11 and the vessel body 21 by shallow covering lids 41, 41 having the same shape and the same size, respectively (FIG. 9(A)). Each lid 41 is formed axially symmetrically right and left and backward and forward. The first vessel 10 and the second vessel 20 can be easily separated from each other by removing one of the engagement part 13 from the engagement groove 23 so that they are relatively inclined horizontally (the direction of the arrow in FIG. 9(B)). FIG. 9(A) and FIG. 9(B) are operation views corresponding the overall perspective view and FIG. 7(B), respectively.

The first vessel 10, the second vessel 20, and the lids 41, 41 are integrally formed, for example, of transparent polystyrene. The first vessel 10 and the second vessel 20 are subjected to a hydrophilization treatment at least on their inner surfaces of the vessel body 11 and the vessel body 21.

The first vessel 10 and the second vessel 20 can be connected via a filter 42 (FIG. 10). The filter 42 is retained on the front face of the opening 22 in such a manner that it is accommodated in the pocket 24a of the guide member 24 of the second vessel 20 (FIG. 10(A)), and can be pushed against the end surface of the vessel body 21 by means of the tip end of the cylindrical member 15 and the partition plate 15a of the first vessel 10, and fixed (FIG. 10(B)). As the filter 42, those having appropriate permeation pore sixes can be selected and used, for example, a membrane filter incorporated in a disposable membrane filter unit (product name "DISMIC"), and "Ultrafilter" (product name) both obtainable from Advantec Toyo Kaisha, Ltd., and the like.

In the first vessel 10 and the second vessel 20, which are not connected with each other, arbitrary cells C1 and cells C2 can be individually cultured in independent culture environments (FIG. 11(A)). At this time, a culture medium $L_1$ and a culture medium $L_2$ are poured into the parts lower than the opening 12 and the opening 22 of the vessel body 11 and the vessel body 21, respectively. When a necessary and sufficient culturing time has lapsed, a secretory substance $E_1$, and a secretory substance $E_2$ from the cells C1, and cells C2 are released into the culture medium $L_1$, and the culture medium $L_2$, respectively. It is to be noted that the cells $C_1$ and the $C_2$ may be the same cell species or may be different cell species. The culture environments of the first vessel 10 and the second vessel 20 may be the same or different from each other. The same also applies to the culture medium $L_1$ and the culture medium $L_2$.

Then the first vessel 10 and the second vessel 20 are connected, and thus the opening 12 and the opening 22 communicate in a watertight manner (FIG. 11(B)). Then a common liquid culture medium $L_3$ is poured into the vessel body 11 and the vessel body 21 to sufficient levels, and thus the secretory substance $E_1$ and the secretory substance $E_2$ in the vessel body 11 and the vessel body 21 communicate each other via the liquid culture medium $L_3$ in the opening 12 and the opening 22, and as the culture time has lapsed, interaction between the cells $C_1$ and the cells $C_2$ is expressed. Therefore, by observing the cells $C_1$ and the cells $C_2$ in the vessel body 11 and the vessel body 21, it is possible to observe and study the interaction between the cells $C_1$ and the cells $C_2$. The culture medium $L_1$ and the culture medium $L_2$ may be the same or different in quality. The liquid culture medium $L_3$ may be the same or different from the culture medium $L_1$ or the culture medium $L_2$ in quality.

Meanwhile, when the first vessel 10 and the second vessel 20 are connected via the filter 43 (FIG. 11(C)), the secretory substance $E_1$ of the large size on the vessel body 11 side fails to move to the vessel body 21 side, and only the secretory substance $E_2$ of the small size on the vessel body 21 side passes through the filter 42 to move into the vessel body 11 side depending on the permeation pore size of the filter 42. This provides effective use for identification and analysis of a causative factor of the interaction between the cells $C_1$ and the cells $C_2$, for example.

The first vessel 10 and the second vessel 20 are not necessarily formed into the same shape and the same size as long as they are the vessel body 11 and the vessel body 21 equipped with the sideways-facing opening 12, and the sideways-facing opening 22 that are connected face to face to communicate in a watertight manner, and may be formed into arbitral shapes including a polygonal shape, other than the rectangular shape or a semicircle shape.

Other Embodiments

In the second vessel 20, the bottom face of the vessel body 21 may be configured by a separate transparent plate 25 (FIG. 12). The transparent plate 25 is bonded to the lower surface of a frame 25a on the periphery of the bottom part of the vessel body 21, and the resultant thinness further facilitates the observation of the culture cells. The transparent plate 25 may be a glass plate or a quartz plate besides a plate of thermoplastic materials. The transparent plate 25 may be a rigid plate, or may be a flexible film. Also regarding the first vessel 10, the bottom face of the vessel body 11 may be configured by a thin transparent plate (not shown). FIG. 12(A) and FIG. 12(B) are a perspective view of the second vessel 20, and a half section of FIG. 12(A), respectively.

The first vessel 10 and the second vessel 20 can be connected via an O ring 43 (FIG. 13). On the side of the inner periphery of the tip end of the cylindrical member 15 of the first vessel 10, a stepped seat part 15b for the O ring 43 is formed. The cylindrical member 15 abuts on the end surface on the opening 22 side of the second vessel 20 via the O ring 43, to allow communication between the opening 12 and the opening 22 in a watertight manner more securely. FIG. 13(A) and FIG. 13(B) are an exploded perspective view, and an enlarged longitudinal section view of the connecting part in FIG. 13(A), respectively.

The first vessel 10 and the second vessel 20 may be connected by pressing the cylindrical member 15 on the first vessel 10 side into a cylindrical member 26 on the second vessel 20 side (FIG. 14). The cylindrical member 26 is formed into a cylindrical shape that surrounds the opening 22. The outer surface of the cylindrical member 15 is formed into a tapered shape having a ring engagement rib 15c in the midway, and the inner surface of the cylindrical member 26 is formed into a tapered shape that fits the outer surface of the cylindrical member 15, and is formed with a ring engagement groove 26a in the midway. The cylindrical member 15 is pressed into the cylindrical member 26, and then the engagement rib 15c comes into engagement with the engagement groove 20a snappingly, and is retained, and the cylindrical member 15 with the engagement rib 15c and the cylindrical member 26 with the engagement groove 26a serve as a connecting mechanism for connecting the first vessel 10 and the second vessel 20. FIG. 14(A) and FIG. 14(B) are an exploded perspective view, and an enlarged longitudinal section view of the connecting part in FIG. 14(A), respectively.

Regarding the first vessel 10 and the second vessel 20, the respective opening 12 and can be closed via films 44, 44 having weak adhesive power (FIG. 15). Each film 44 is weakly adhered on the inner surface side of the vessel body 11 or the vessel body 21 so that it can be stripped, to thereby close the opening 12 and the opening 22. Each film 44 is preferably weakly adhered, for example, by thermal adhesion without using an adhesive or a pressure sensitive adhesive for preventing harmful contamination. FIG. 15(A) is an overall perspective view, and FIG. 15(B) and FIG. 15(C) are schematic operation explanatory diagrams, respectively.

To each of the first vessel 10 and the second vessel 20, a sufficient amount of the liquid culture medium $L_3$ is poured at the same level (the upper view in FIG. 15(B)), and the respective films 44, 44 are removed simultaneously (the lower view in FIG. 15(B)), and thus the liquid culture medium $L_3$ can be communicated in both directions through the opening 12 and the opening 22. Also by pouring the liquid culture medium $L_3$ into the first vessel 10 and the second vessel 20 at different levels (the upper view in FIG. 15(C)), and removing the respective films 44, 44 simultaneously (the lower view in FIG. 15(C)), it is possible to allow the liquid culture medium $L_3$ on the higher level side to flow into the lower level side through the opening 12 and the opening 22 to level with each other. In both cases, the communication timing between the first vessel 10 and the second vessel 20 by the liquid culture medium $L_3$ can be strictly defined, so that it is convenient for specifically observing, the time-varying data of the interaction between cells cultured in the first vessel 10 and the second vessel 20, for example. In comparison with the case of additionally pouring the liquid culture medium $L_3$ into the first vessel 10 and the second vessel 20 from outside, the problems of disturbance on the cells cultured in the first vessel 10 and the second vessel 20, and dilution of the secretor factor from culture cells can be reduced.

The opening 12 and the cylindrical member 15 of the first vessel 10 may foe provided with a vertical partition plate 15d on the horizontal partition plate 15a, and the opening 22 of the second vessel 20 may be provided with a vertical supporting rod 27 for the filter 42 (FIG. 16).

The partition plate 15d has the same length with the cylindrical member 15 and the partition plate 15a, and the width of the supporting rod 27 is the same with the plate thickness of the partition plate 15d. The supporting rod 27 stands slightly backward from the end surface on the opening 22 side of the vessel body 21, and the surface of the supporting rod 27 is formed with horizontal ribs 27a, 27a having a conical section, and each horizontal rib 27a has such a height that the apex coincides with the end surface of the vessel body 21. The filter 42 that is retained on the front face of the opening 22 via the pocket 24a of the guide member 24 can be stably supported on the front surface of the opening 22 via the cylindrical member 15, the partition plate 15a, the partition plate 15d, and the horizontal rib 27a, 27a of the supporting rod 27 without accompanied by reduction of substantial permeation area. FIG. 16(A) and FIG. 16(B) are an exploded perspective view, and an enlarged longitudinal section view of the connecting part in FIG. 16(A), respectively.

The supporting rod 27 is not necessarily made into correspondence with the partition plate 15d as long as it can support the filter 42 on the front surface of the opening 22 together with the cylindrical member 15, the partition plate 15a, and the partition plate 15d, and two or more supporting rods 27 may be provided while they are tilted in the direction other than the vertical direction. The supporting rod 27 may have on its surface a rib, a protrusion and the like of an arbitrary form other than those illustrated in the drawing, in place of the horizontal rib 27a.

Regarding the first vessel 10 and the second vessel 20, the vessel body 11 and the vessel body 21 may be divided in two in the right and left direction by a longitudinally disposed partition plate 10 and a partition plate 28 of the vessel body 11 and the vessel body 21 (FIG. 17). In FIG. 17, the partition plate 16 is formed integrally with the vertical partition plate 15d that divides the opening 12 and the cylindrical member 15 in two, and divides the interior of the vessel body 11 together with the opening 12 in two in the right and left direction from the bottom face to the upper end part, and the partition plate 28 divides the interior of the vessel body 21 together with the opening 22 in two in the right and left direction. That is, the partition plate 16 and the partition plate 28 are able to divide the vessel body 11 and the vessel body 21 respectively into two rooms, which are especially convenient, for example, for the use such as a comparison test between different cell species cohered in same condition in the respective rooms.

The first vessel 10 and the second vessel 20 can be connected via a third vessel 30 (FIG. 18). On one end surface of a rectangular box-shaped vessel body 31 of the third vessel 30, an opening 32, a guide member 34, and right and left engagement grooves 35, 35 having the same shapes and sizes with the opening 22, the guide member 24, and the right and left engagement groove 23, 23 of the second vessel 20 are formed. Also on the other end surface of the vessel body 31 of the third vessel 30, an opening 36, a cylindrical member 37 with a partition plate 37a, and right, and left engagement parts 33, 33 having the same shapes and sizes with the opening 12, the cylindrical member 15 with the partition plate 15a, and the right and left engagement parts 13, 13 of the first vessel 10 are formed. That is, the vessel body 31 of the third vessel 30 is provided with a pair of the sideways-facing opening 32 and the sideways-facing opening 36 symmetrically. In FIG. 18, the cylindrical member 15 and the cylindrical member 37 are not shown, and either one is shown with regard to the engagement grooves 23, 23, 35 and 35. The vessel body 31 is formed into a rectangular shape having the same size with the vessel body 11 and the vessel body 21.

Cells can be cultured individually in the first vessel 10, the second vessel 20 and the third vessel 30, and these vessels can be connected with each other to observe the interactions between three or more species of cultured cells (FIG. 19). FIG. 19 shows the form in which the first vessel 10 and the second vessel 20 are connected via two third vessels 30, 30. That is, the number of the third vessel 30 to be interposed between the first vessel 10 and the second vessel 20 can be an arbitrary value of more than or equal to 1.

In the first vessel 10, the second vessel 20 and the third vessel 30, the interiors of the vessel body 11, the vessel body 21, and the vessel body 31 respectively can be divided into three by partition plates 17, 17, partition plates 29, 29, and partition plate 38, 38 (FIG. 20).

On one end surface of each room of the first vessel 10, the opening 12, and the cylindrical member 15 with the partition plate 15a are formed, and on one end surface of each room of the second vessel 20, the opening 22, and the guide member 24 are formed. Also, on one end surface of each room of the third vessel 30, the opening 32, and the guide member 34 are formed, and on the other end surface, the opening 36, and the cylindrical member 37 with the partition plate 37a are formed. On the right and left of the end surface on the side of the openings 12, 12 of the first vessel 10, the engagement parts 13, 13 are formed, and on the right and left lateral walls of the end surface on the side of the openings 22, 22 of the second vessel 20, the engagement grooves 23, 23 are formed. On the right and left lateral walls of the end surface on the side of the openings 32, 32 of the third vessel 30, the engagement grooves 35, 35 are formed, and on the right and left of the end surface on the side of the openings 36, 36, the engagement parts 33, 33 are formed. That is, in the first vessel 10 and the second vessel 20, the sideways-facing opening 12 and the sideways-facing opening 22 are formed for each room, and in the third vessel 30, a pair of the sideways-facing opening 32 and the sideways-facing opening 36 is formed symmetrically for each room. In FIG. 20, the cylindrical member 15 and the cylindrical member 37 are not shown, and each one of the engagement grooves 23, 23, 35 and 35 are shown.

In the first vessel 10, the second vessel 20 and the third vessel 30, cells are individually cultured by using different rooms, and the vessels are connected with each other to enable observation of the interactions between cultured cells of more than or equal to 3×n species (FIG. 21). Since each room of the first vessel 10 and the second vessel 20 has the opening 12 and the opening 22, respectively, and each room of the third vessel 30 has the opening 32 and the opening 36, for example, by retaining an appropriate filter on the front face of each opening 22 and opening 32, it is possible to conduct an extensive comparison test according to the secretor factors from the culture cells at once. The number of the third vessel 30 to be interposed between the first vessel 10 and the second vessel 20 is n≥1, and FIG. 21 illustrates the form in which n=2. In FIG. 20 and FIG. 21, each of the first vessel 10, the second vessel 20, and the third vessel 30 may be divided into a two or more multiple rooms.

Each of the vessel body 11 and the vessel body 21 of the first vessel 10 and the second vessel 20 can be formed into a closed-bottom cylinder (FIG. 22). FIG. 22(A) and FIG. 22(B) are an exploded perspective view, and a perspective view of the connected state, respectively.

In the first vessel 10, the cylindrical member 15 with the partition plate 15a that surrounds the sideways-facing opening 12 is attached with the engagement parts 13, 13 with inward engagement ribs 13a for connecting with the second vessel 20 on the right and left. On the tip outer periphery side of the cylindrical member 15, the stepped seat part 15b for the O ring 43 is formed. Meanwhile, in the second vessel 20, the cylindrical member 28 surrounding the sideways-facing opening 22 is formed with a partition plate 28b corresponding to the partition plate 15a of the cylindrical member 15, and the tip end of the cylindrical member 26 is formed with the O ring 43, and the circular guide member 24 for accommodating the tip end part of the cylindrical member 15 to position it. On the right and left of the guide member 2 engagement blocks 23d, 23d corresponding to the engagement parts 13 on the side of the first vessel 10 are formed, and the engagement parts 13, 13 can come into engagement with the engagement blocks 23d, 23d snappingly via the engagement ribs 13a, 13a in the tip end part of the engagement parts 13, 13, thereby connecting the first vessel 10 and the second vessel 20 detachably. That is, the engagement parts 13, 13, and the engagement blocks 23d, 23d serve as a connecting mechanism for connecting the first vessel 10 and the second vessel 20 to communicate the opening 12 and the opening 22 in a watertight manner.

By accommodating and retaining the filter 42 in the guide member 24 in connecting the first vessel 10 and the second vessel 20 (two-dot chain line in FIG. 22(A)), it is possible to retain the filter 12 on the front face of the opening 22, and to communicate the opening 12 and the opening 22 via the filter 42. In the first vessel 10 and the second vessel 20 in FIG. 22, various options for the box-shaped vessel body 11 and vessel body 21, for example, in FIG. 15 to FIG. 17 can be applied, and one or a combination of two or more third vessel 30 of the closed-bottom cylindrical vessel body 31 may be used following FIG. 18 and FIG. 19. Each of the first vessel 10 and the second vessel 20 can be closed from above by a covering lid (not shown) in the connected state of FIG. 22(B).

In the above description, the first vessel 10 and the second vessel 20, without combined with the third vessel 30, or in combination with the third vessel 30, can be desirably used not only for the purpose of cell culture but also for experimental and research purposes including culture, regeneration, manufacture, observation and the like of targets such as cells, organs, and microorganisms.

The present application claims the benefit of the priority date of Japanese patent application No. 2013-164907 filed on Aug. 8, 2013 and No. 2014-135535 filed on Jul. 1, 2014. All of the contents of the Japanese patent application No. 2013-164907 and No. 2014-135535 are incorporated by reference.

INDUSTRIAL APPLICABILITY

The present invention can be broadly applied to the experimental and research purposes including culture, regeneration, manufacture, observation and the like of targets such as cells, organs, and microorganisms.

DESCRIPTION OF THE NUMERALS 10 first vessel
12 opening
15 cylindrical member
20 second vessel
22 opening
24 guide member
25 transparent plate
27 supporting rod
30 third vessel
32, 36 opening
42 filter
44 film

The invention claimed is:
1. A culture vessel comprising a first vessel and a second vessel each formed of a transparent thermoplastic material,
wherein the first vessel has a first sideways-facing opening, a first closed bottom, and a first open top, and
wherein the second vessel has a second sideways-facing opening, a second closed bottom, and a second closed top, and
(1) the first vessel is formed with a cylindrical member projecting outwardly that surrounds the first sideways-facing opening,
(2) the second vessel is formed with a protruding guide member for positioning the cylindrical member when the second vessel is connected with the first vessel,
(3) a first connector is formed on the first vessel and a second connector is formed on the second vessel,
wherein the first connector comprises a first engagement part comprising one or more engagement ribs and a second engagement part comprising one or more engagement ribs, the first engagement part extending from an end surface to a right side of the first sideways-facing opening on the first vessel, and the second engagement part extending from an end surface to a left side of the first sideways-facing opening on the first vessel, and
wherein the second connector comprising engagement grooves or engagement blocks,
(4) the first closed bottom and the second closed bottom are transparent plates, and
(5) the first sideways-facing openings and the second sideways-facing opening communicate in a watertight manner when the first sideways-facing opening and the second sideways-facing opening are connected face to face via the first connector and the second connector.
2. The culture vessel according to claim 1, wherein the first sideways-facing opening is formed into a semicircle with the circular arc upside, and wherein the second sideways-facing opening is formed into a semicircle with the circular arc upside.

3. The culture vessel according to claim 1, wherein, in the second vessel, a filter is retained on the front face of the second sideways-facing opening.

4. The culture vessel according to claim 3, wherein, in the second vessel, the second sideways-facing opening is provided with a supporting rod for supporting the filter.

5. The culture vessel according to claim 1, wherein the first sideways-facing opening is closed via a strippable film, and wherein the second sideways-facing opening is closed via a strippable film.

6. The culture vessel according to claim 1, wherein the first vessel has an interior that together with the opening is divided into two rooms, and wherein the second vessel has an interior that together with the opening is divided into two rooms.

7. The culture vessel according to claim 1, wherein the first vessel and the second vessel are connected via a third vessel that has a pair of symmetrical sideways-facing openings.

8. The culture vessel according to claim 7, wherein the first vessel has an interior that together with the opening is divided into multiple rooms, wherein the second vessel has an interior that together with the opening is divided into multiple rooms, and wherein the third vessel has an interior that together with the opening is divided into multiple rooms.

9. A culture vessel comprising a first vessel and a second vessel each formed of a transparent thermoplastic material,
wherein the first vessel has a first sideways-facing opening, a first closed bottom, and a first open top, and
wherein the second vessel has a second sideways-facing opening, a second closed bottom, and a second closed top, and
(1) the first vessel is formed with a cylindrical body projecting outwardly that surrounds the first sideways-facing opening, wherein the cylindrical body comprises an engagement part with an engagement rib on a right side and an engagement part with an engagement rib on a left side,
(2) the second vessel is formed with a cylindrical member with an engagement groove,
(3) a first connector is formed on the first vessel and a second connector is formed on the second vessel, wherein the first connector is the cylindrical body, and the second connector is the cylindrical member with the engagement groove,
(4) the first closed bottom and the second closed bottom are transparent plates, and
(5) the first sideways-facing opening and the second sideways-facing opening communicate in a watertight manner when the first sideways-facing opening and the second sideways-facing opening are connected face to face via the first connector and the second connector.

* * * * *